(12) United States Patent
Takayama et al.

(10) Patent No.: US 11,022,431 B2
(45) Date of Patent: Jun. 1, 2021

(54) SHAPE CALCULATING APPARATUS

(71) Applicant: OLYMPUS CORPORATION, Tokyo (JP)

(72) Inventors: Koichi Takayama, Koganei (JP); Hiromasa Fujita, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 429 days.

(21) Appl. No.: 15/945,910

(22) Filed: Apr. 5, 2018

(65) Prior Publication Data

US 2018/0224269 A1 Aug. 9, 2018

Related U.S. Application Data

(63) Continuation of application No. PCT/JP2015/078227, filed on Oct. 5, 2015.

(51) Int. Cl.
*G01B 11/245* (2006.01)
*G01B 11/16* (2006.01)
(Continued)

(52) U.S. Cl.
CPC ........ *G01B 11/245* (2013.01); *A61B 1/00006* (2013.01); *A61B 1/00009* (2013.01);
(Continued)

(58) Field of Classification Search
CPC combination set(s) only.
See application file for complete search history.

(56) References Cited

U.S. PATENT DOCUMENTS 6,127,672 A * 10/2000 Danisch ................ G01B 11/18
250/227.14
6,389,205 B1 * 5/2002 Muckner ............ A61B 1/00117
362/574
(Continued)

FOREIGN PATENT DOCUMENTS

| JP | 2007-44410 A | 2/2007 |
| JP | 4714570 B2 | 6/2011 |
| JP | 2015-29831 A | 2/2015 |

OTHER PUBLICATIONS

International Search Report dated Dec. 28, 2015 received in PCT/JP2015/078227.
(Continued)

*Primary Examiner* — Anh Tuan T Nguyen
*Assistant Examiner* — Shankar Raj Ghimire
(74) *Attorney, Agent, or Firm* — Scully, Scott, Murphy & Presser, P.C.

(57) ABSTRACT

A shape calculating apparatus includes a light source and a light guide provided with detection targets to decrease quantity of light guided by the light guide according to a bend shape of the light guide. The apparatus also includes a light detector to detect light quantity information in wavelengths included in light absorption spectra of the detection targets, a calculation unit that makes a calculation relating to a shape of each detection target based on the light quantity information, and a control unit that changes a dynamic range of at least one of an intensity of light input to the light guide and a detection signal output by the light detector for each wavelength range so that a magnitude of the detection signal is within a range between a lower limit threshold and an upper limit threshold of the light detector.

25 Claims, 25 Drawing Sheets

(51) Int. Cl.
  *A61B 1/07* (2006.01)
  *A61B 1/06* (2006.01)
  *A61B 1/00* (2006.01)

(52) U.S. Cl.
  CPC ...... *A61B 1/00126* (2013.01); *A61B 1/00165* (2013.01); *A61B 1/00186* (2013.01); *A61B 1/00195* (2013.01); *A61B 1/0646* (2013.01); *A61B 1/07* (2013.01); *G01B 11/18* (2013.01); *A61B 1/0002* (2013.01)

(56) References Cited

U.S. PATENT DOCUMENTS

| | | | | |
|---|---|---|---|---|
| 6,563,107 | B2 * | 5/2003 | Danisch | G01B 11/18 250/227.14 |
| 6,846,286 | B2 * | 1/2005 | Suzuki | A61B 1/00071 600/117 |
| 7,099,056 | B1 * | 8/2006 | Kindt | H04N 5/2351 348/96 |
| 7,440,661 | B2 | 10/2008 | Kobayashi | |
| 2001/0052930 | A1 * | 12/2001 | Adair | A61B 1/00016 348/65 |
| 2007/0116415 | A1 * | 5/2007 | Kobayashi | A61B 5/065 385/116 |
| 2007/0225560 | A1 * | 9/2007 | Avni | A61B 1/0684 600/118 |
| 2013/0016200 | A1 * | 1/2013 | Ovod | A61B 1/06 348/68 |
| 2014/0036261 | A1 * | 2/2014 | Fujita | G02B 6/02052 356/300 |
| 2015/0238086 | A1 * | 8/2015 | Saito | A61B 1/0638 600/339 |
| 2016/0128552 | A1 | 5/2016 | Tojo et al. | |

OTHER PUBLICATIONS

English translation of International Preliminary Report on Patentability dated Apr. 19, 2018 together with the Written Opinion received in related International Application No. PCT/JP2015/078227.

* cited by examiner

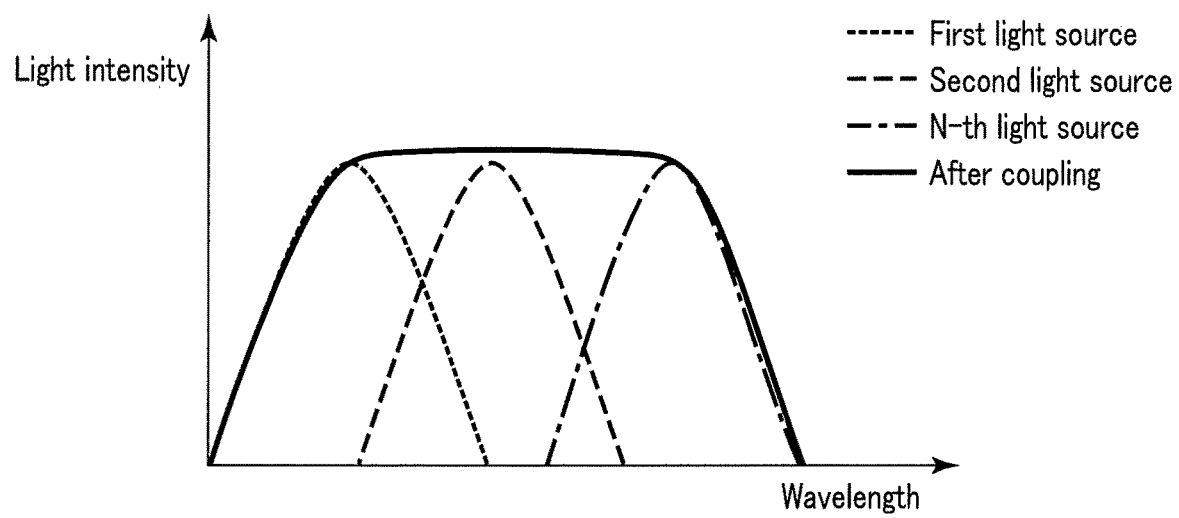
F I G. 3
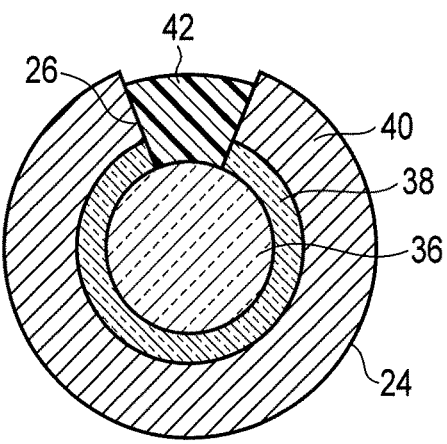
F I G. 4
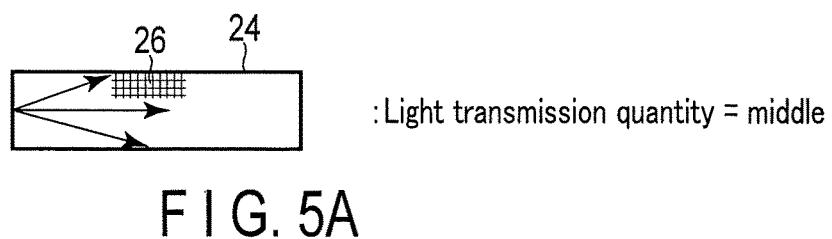
F I G. 5A

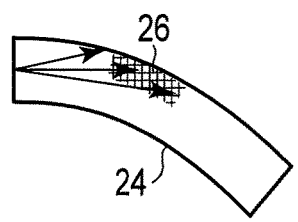
: Light transmission quantity = small
F I G. 5B
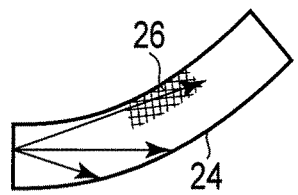
: Light transmission quantity = large
F I G. 5C
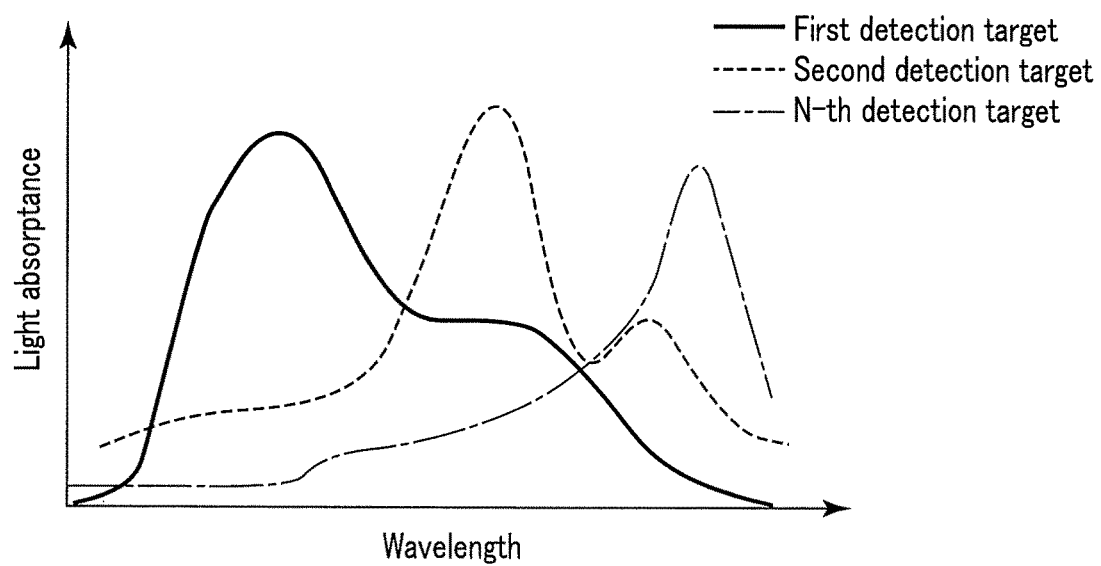
F I G. 6

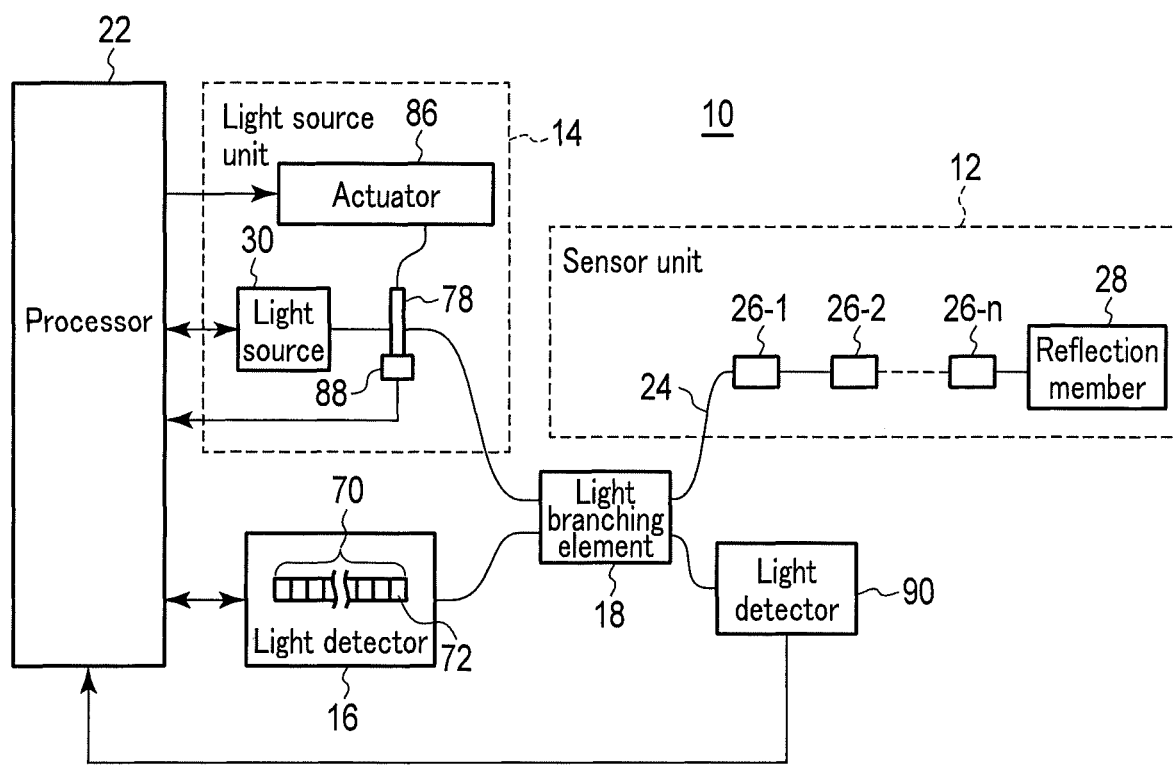
F I G. 27

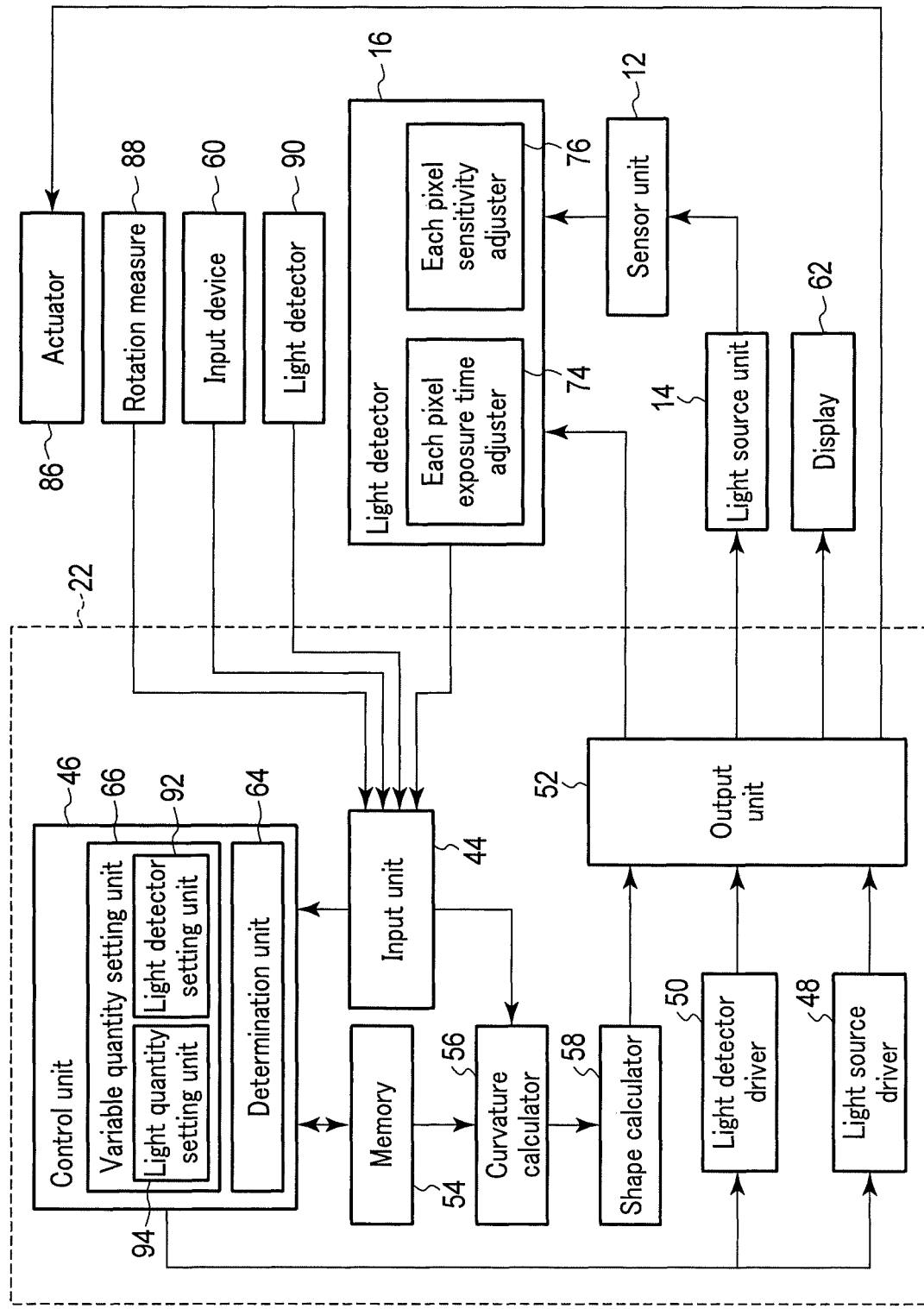
F I G. 28

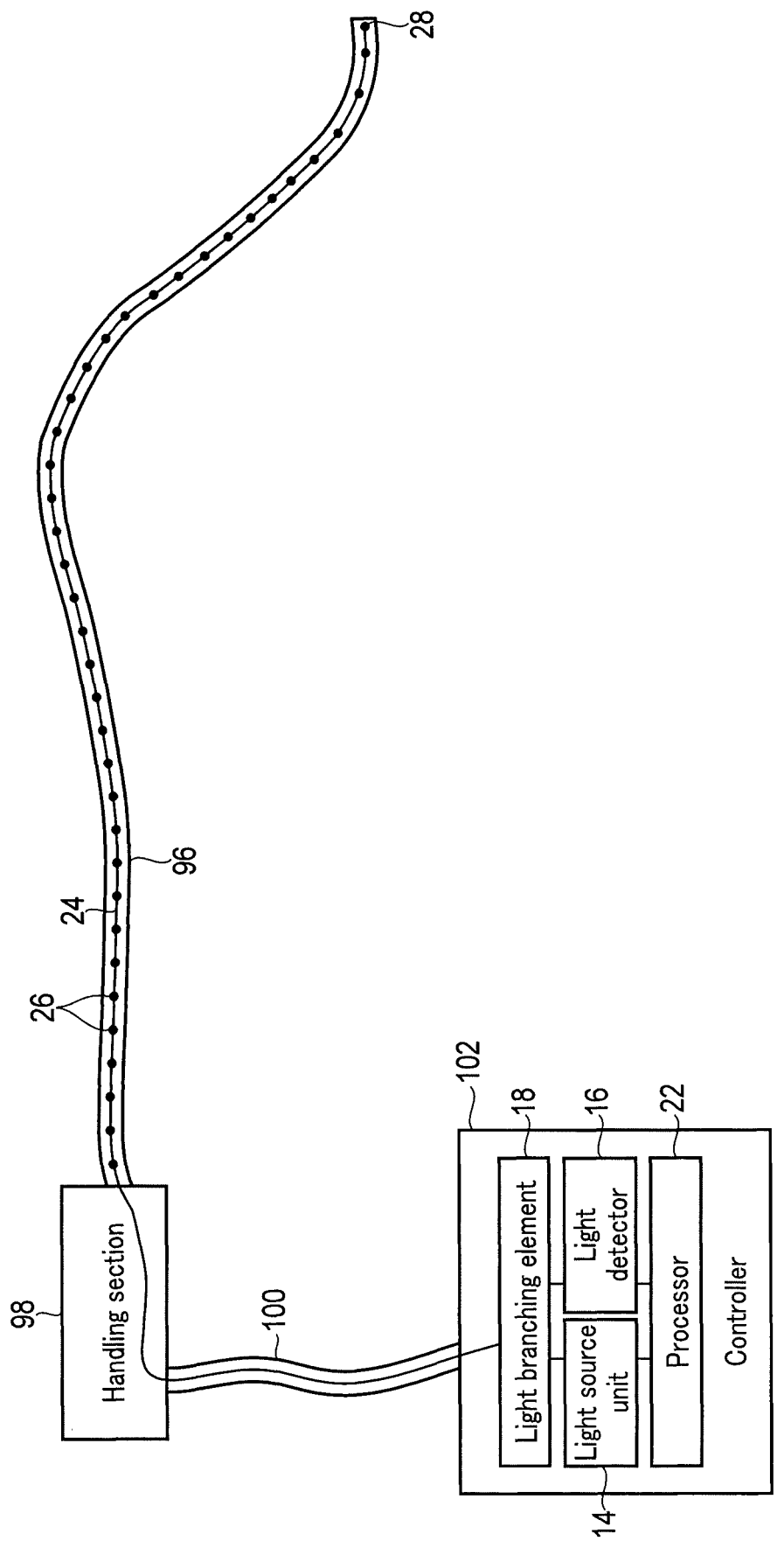
F I G. 31

SHAPE CALCULATING APPARATUS

CROSS REFERENCE TO RELATED APPLICATIONS

This application is a continuation application of PCT Application No. PCT/JP2015/078227 filed on Oct. 5, 2015, the entire contents of which are incorporated herein by reference.

BACKGROUND OF THE INVENTION

1. Field of the Invention

The present invention relates to a shape calculating apparatus that calculates a shape of each of detection targets by use of light quantity information indicating a relationship between a wavelength corresponding to each of the detection targets and a light quantity detected about the wavelength, which has been obtained by a sensor configured to sense the light quantity that differs according to the shape of each of detection targets.

2. Description of the Related Art

Japanese Patent No. 4714570 discloses an endoscope shape detection probe that bends together with a scope as one piece and detects a shape of the scope. This detection probe includes, as a detection target provided in a fiber for curvature detection, a light modulator to change light quantity in accordance with a curvature. The detection probe configured in such a manner is capable of detecting the shape of the scope on the basis of the intensity or wavelength of light modulated by the light modulating unit and the distance between the light modulator and an output end of the curvature detection use fiber.

Japanese Patent No. 4714570 also discloses that detection targets corresponding to wavelength components different from one another are provided in the fiber for curvature detection, which allows detecting not only a shape of a portion of the scope, but also the shapes of various portions of the scope over a desired length.

BRIEF SUMMARY OF THE INVENTION

A shape calculating apparatus includes: a light source that emits light; a light guide that is disposed in a structure to be a target for shape calculation and guides light emitted from the light source; detection targets that are disposed in the light guide in a longitudinal direction of the light guide, have light absorption spectra different from one another, and absorb light guided by the light guide according to a bend shape of the light guide to decrease light quantity; a light detector that detects light quantity information in wavelengths included in the light absorption spectra in the light guided by the light guide to output a detection signal; a calculation unit that makes a calculation relating to a shape of each of the detection targets based on the light quantity information; and a control unit that changes a dynamic range of at least one of an intensity of light input to the light guide and the detection signal output by the light detector for each of predetermined wavelength ranges so that a magnitude of the detection signal is within a range between a lower limit threshold relating to a lower detection limit of the light detector and an upper limit threshold relating to an upper detection limit of the light detector.

Additional objects and advantages of the invention will be set forth in the description that follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 3 is a view showing a light intensity spectrum of each light source of the light source unit.

FIG. 4 is a cross-sectional view of a portion of a light guide where a detection target is provided.

FIG. 5A is a view showing a light transmission quantity when the light guide is not bent.

FIG. 5B is a view showing a light transmission quantity when the light guide is bent toward a side opposite to the side where the detection target is provided.

FIG. 5C is a view showing a light transmission quantity when the light guide is bent toward the side where the detection target is provided.

FIG. 6 is a graph showing a light absorption spectrum of each detection target.

FIG. 27 is a view showing a schematic configuration of a shape calculating apparatus according to a fourth embodiment of the present invention.

FIG. 28 is a block diagram showing a functional configuration of a processor and its peripheral parts of the shape calculating apparatus according to the fourth embodiment.

FIG. 31 is a block diagram showing a schematic configuration of an endoscope apparatus mounted with a shape calculating apparatus according to any of the embodiments.

DETAILED DESCRIPTION OF THE INVENTION

The embodiments for executing the present invention will be described below with reference to the drawings.

First Embodiment

Figure 1:
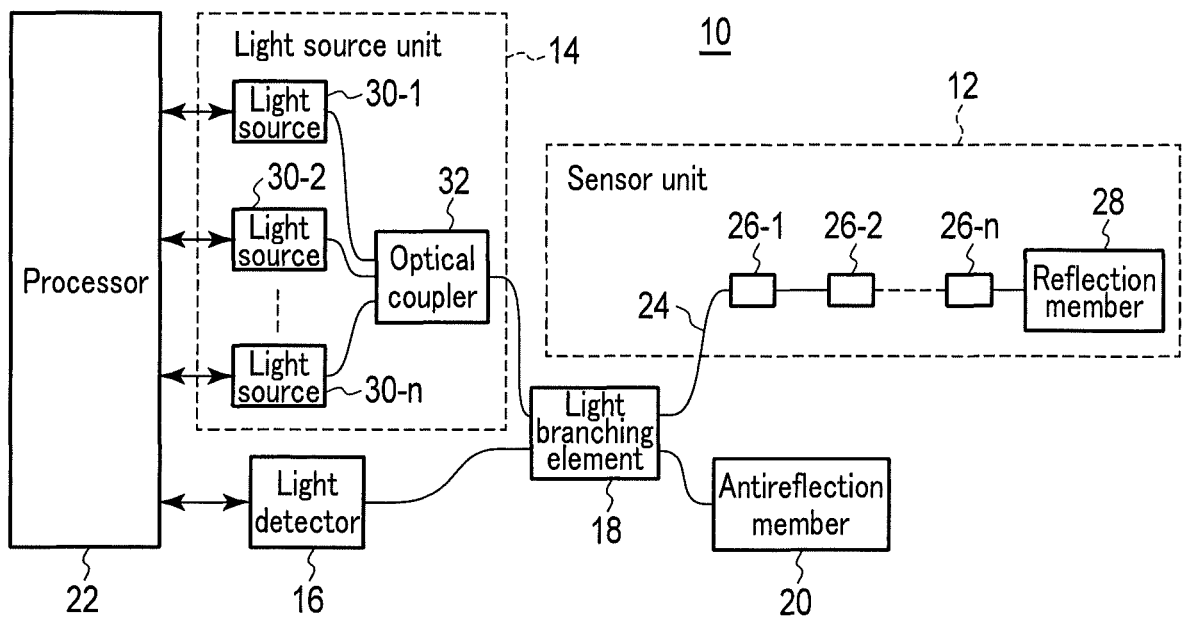
FIG. 1 is a view showing a schematic configuration of a shape calculating apparatus according to a first embodiment of the present invention.

As shown in FIG. 1, a shape calculating apparatus 10 according to the present first embodiment is constituted by a sensor unit 12, a light source unit 14, a light detector 16, a light branching element 18, an antireflection member 20, and a processor 22. The sensor unit 12 is constituted by a light guide 24, n detection targets 26 (the first detection target 26-1, the second detection target 26-2, . . . , and the n-th detection target 26-n), and a reflection member 28.

The light source unit 14 is constituted by n light sources 30 (the first light source 30-1, the second light source 30-2, . . . , and the n-th light source 30-n), and an optical coupler 32.

Figure 2:
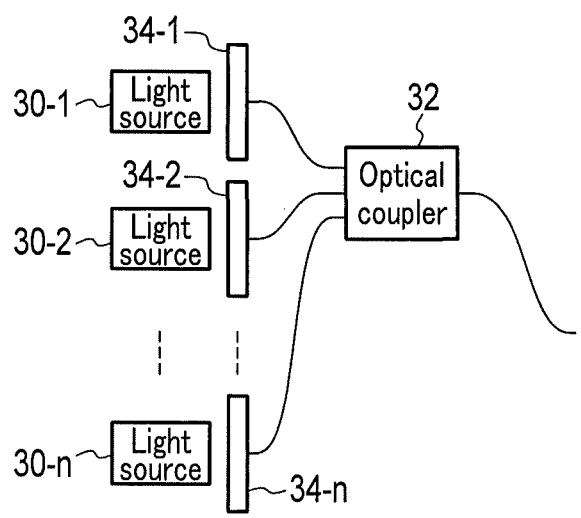
FIG. 2 is a view showing a configuration example of a light source unit.

For each light source 30, light of a laser diode (LD), an LED, a lamp, etc., or the light emitted from a fluorescent material by the aforementioned light can be used. The light sources 30-1, 30-2, . . . , and 30-n differ from one another in optical frequency spectrum. Even if the optical frequency spectra of the light sources 30-1, 30-2, . . . , and 30-n are the same, they may be changed by respectively disposing the first optical filter 34-1, the second optical filter 34-2, . . . , and the n-th optical filter 34-*n* whose absorptivities are different in front of the light sources 30 as shown in FIG. 2. The light intensity of each light source 30 is controlled by the processor 22.

The optical coupler 32 couples the light from the n light sources 30. The light intensity of each light source and that of the coupled light are shown in FIG. 3. In that manner, the light source unit 14 prepares light of a wavelength characteristic necessary for the shape calculating apparatus 10 (e.g., white light) by the combination of n light, and emits the coupled light.

The light branching element 18 is constituted by, for example, a fiber coupler, a half mirror, or a beam splitter, and causes the light emitted from the light source unit 14 to enter one end of the light guide 24. When the light branching element 18 is a fiber coupler, the light source unit 14 includes a lens system that converges light to cause it to enter a fiber of the fiber coupler, etc. When the light branching element 18 is a half mirror or a beam splitter, the light source unit 14 includes a lens system or the like that collimates light into a parallel beam of light. Furthermore, when an output is influenced by a returning light as in a laser diode, the light source unit 14 includes an isolator, etc.

The light guide 24 guides the light that has entered the one end of the light guide 24 by the light branching element 18 to the other end, and radiates the light from the other end. The reflection member 28 reflects the light radiated from the other end of the light guide 24, and once again causes the light to enter the other end of the light guide 24. Thereby, the light guide 24 guides the light that has entered the other end to the one end, and radiates the light from the one end. The light branching element 18 inputs the light radiated from the one end of the light guide 24 into the light detector 16. The light detector 16 detects quantities of light of predetermined wavelengths in the input light, and outputs light quantity information indicating a relationship between the wavelengths and the light quantities into the processor 22. The light detector 16 can include, for example, a line sensor constituted by pixel sensors that measure the light intensities of wavelength ranges different from one another.

The antireflection member 20 is used to prevent light that has not entered the light guide 24 from returning to the light detector 16.

Here, the light guide 24 is disposed to extend along the longitudinal direction of a structure on which curvature information should be detected by the shape calculating apparatus 10, such as an insertion section of an endoscope, and has flexibility to bend by following the bend state of the structure.

Specifically, the light guide 24 can be constituted by an optical fiber. FIG. 4 shows the configuration of the cross section of this optical fiber in the radial direction orthogonal to the longitudinal axis direction. That is, the optical fiber is constituted by a core 36 existing in the center of the optical fiber that guides light, a cladding 38 provided around the core 36 that stably confines light in the core 36, and a jacket 40 for protecting the core 36 and the cladding 38 from physical and thermal impacts.

The light guide 24 is not restricted to an optical fiber, but may be constituted by a light waveguide.

In the light guide 24, in the portions corresponding to the positions of the structure on which curvature information should be detected, the detection targets 26 (the first detection target 26-1, the second detection target 26-2, ..., and the n-th detection target 26-*n*) whose light absorption spectra differ from one another are provided. Here, curvature information is the information on the direction and magnitude of a bend.

If the curvature of the light guide 24 is changed, the quantity of light being guided by the light guide 24 varies. FIGS. 5A, 5B, and 5C are pattern diagrams showing light transmission quantities according to a bend of the light guide 24. Here, FIG. 5A shows a light transmission quantity when the light guide 24 is not bent, FIG. 5B shows a light transmission quantity when the light guide 24 is bent toward a side opposite to the side where the detection target 26 is provided, and FIG. 5C shows a light transmission quantity when the light guide 24 is bent toward the side where the detection target 26 is provided. As shown in FIGS. 5A, 5B, and 5C, the light transmission quantity is largest when the light guide 24 is bent toward the side where the detection target 26 is provided, is less when the light guide 24 is not bent, and is smallest when the light guide 24 is bent toward the side opposite to the side where the detection target 26 is provided. Accordingly, by measuring the light intensity of an optical signal output from the light guide 24, the bend degree at the detection target 26 can be detected. Since the position in the radial direction where the detection target 26 is provided in the light guide 24, that is, the direction of the detection target 26, is already-known, the bend direction can also be known. Curvature information can be detected by this bend direction and the bend degree.

The detection target 26 is, as shown in FIG. 4, for example, formed by removing the jacket 40 and the cladding 38 to expose a portion of the core 36 in a desired position in the longitudinal axis direction of the light guide 24, and, in the exposed portion of the core 36, filling a detection target material 42 in a thickness of recovering the original figure of the light guide 24. The detection target material 42 is constituted by an optical characteristic changing material that exerts an optical influence different from the other detection targets 26 on the spectrum of light striking it according to the bend degree in a particular direction. The detection target material 42 is made of materials with a low-refractive index, for example, flexible or elastic materials such as a resin of acrylic, epoxy, silicon, fluorine, etc., and a soft water glass. It is also possible to form the detection target material 42 to be thick to the approximately same degree of the cladding thickness, and fill a material for the jacket 40 in the portion where the jacket 40 and the cladding 38 are removed on the detection target material 42 to recover the original figure of the light guide 24.

The removal of the jacket 40 and the cladding 38 is conducted by laser processing, or by use of a masking process, an etching process, etc. At this time, if the core 36 is damaged at the micro level, the light guide 24 will lose a guiding light by light leakage, or will be vulnerable to bends. Thus, a processing method with minimal damage to the core 36 is desirable.

As an optical characteristic changing material that constitutes the detection target material 42, a light absorber whose light absorption spectrum differs in each detection target 26 as shown in FIG. 6 is possible. That is, since, in each detection target 26, a predetermined wavelength region is absorbed, if the quantity of light of the wavelength in the wavelength region is detected, the bend degree of the detection target 26 can be obtained on the basis of the light quantity.

Alternatively, the detection target material 42 may be constituted by an optical characteristic changing material composed of metallic particles that absorb light in a predetermined wavelength region. This optical characteristic changing material composed of metallic particles has a special spectroscopic absorption spectrum different from the spectroscopic absorption spectrum inherent in the metal. This optical characteristic changing material composed of metallic particles has, for example, the photoexcitation plasmon generation function that can excite a plasmon by light from at least a type of light source. That is, the metallic particles are metallic nanoparticles that include the sum of a spectroscopic absorption spectrum inherent in metal and a special absorption spectrum by a surface plasmon effect as an absorption spectrum. The photoexcitation plasmon generation function is obtainable from any of at least a type of plasmon substance, a nano-sized substance, a nano-sized mineral, and a nano-sized metal. Here, a plasmon substance is a substance in which free electrons collectively vibrate, and behave as pseudo particles. "Nano-sized" means being less than 1 μm. The metallic particles are, for example, Au, Ag, Cu, and Pt, and are a dispersion medium. The figure of each metallic particle is a sphere, a column, or a prism.

Regarding the photoexcitation plasmon generation function, if at least one of the size, length, and thickness of, for example, the same metallic particles of the same optical characteristic changing material is different, its special spectroscopic absorption spectrum differs. For example, as the particle size gets bigger, the peak wavelength of optical absorptivity (absorption wavelength characteristic region) moves toward longer wavelengths. Accordingly, the optical characteristic changing materials of the detection targets 26 can be constituted by the same metallic element, but have different special spectroscopic absorption spectra.

In addition, regarding the photoexcitation plasmon generation function, if, for example, the metallic particles of the optical characteristic changing material are different, its special spectroscopic absorption spectrum differs.

Furthermore, a compound optical characteristic changing material composed of the mixture of different types of metallic particles can also be used.

Accordingly, by using, optical characteristic changing materials, for example, metallic particles, at least one of the size, length, and thickness of each of which is made different, the detection target materials 42 having special spectroscopic absorption spectra different from one another can be obtained. A number of the detection targets 26 that make optical characteristic changes different from one another in light can be formed.

As an optical characteristic changing material, an optical characteristic changing material including laminated dielectric films, an optical characteristic changing material including a fluorescent substance, and an optical characteristic changing material in a grating structure are also possible, for example.

In the shape calculating apparatus 10 configured as above, light enters the light guide 24 from the light source unit 14 through the light branching element 18. The light that has entered is reflected by the reflection member 28 at a distal end of the light guide 24. The reflected light is received by the light detector 16 through the light branching element 18. The light received by the light detector 16 is the light that has passed through the detection targets 26 (the first detection target 26-1, the second detection target 26-2, . . . , and the n-th detection target 26), and differs according to the curvature of the light guide 24. The quantity of light received by the light detector 16 and having the wavelength relating to each detection target 26 is given to the processor 22 as light quantity information (Dλn), and the processor 22 calculates curvature information on the basis of this light quantity information.

Figure 7:
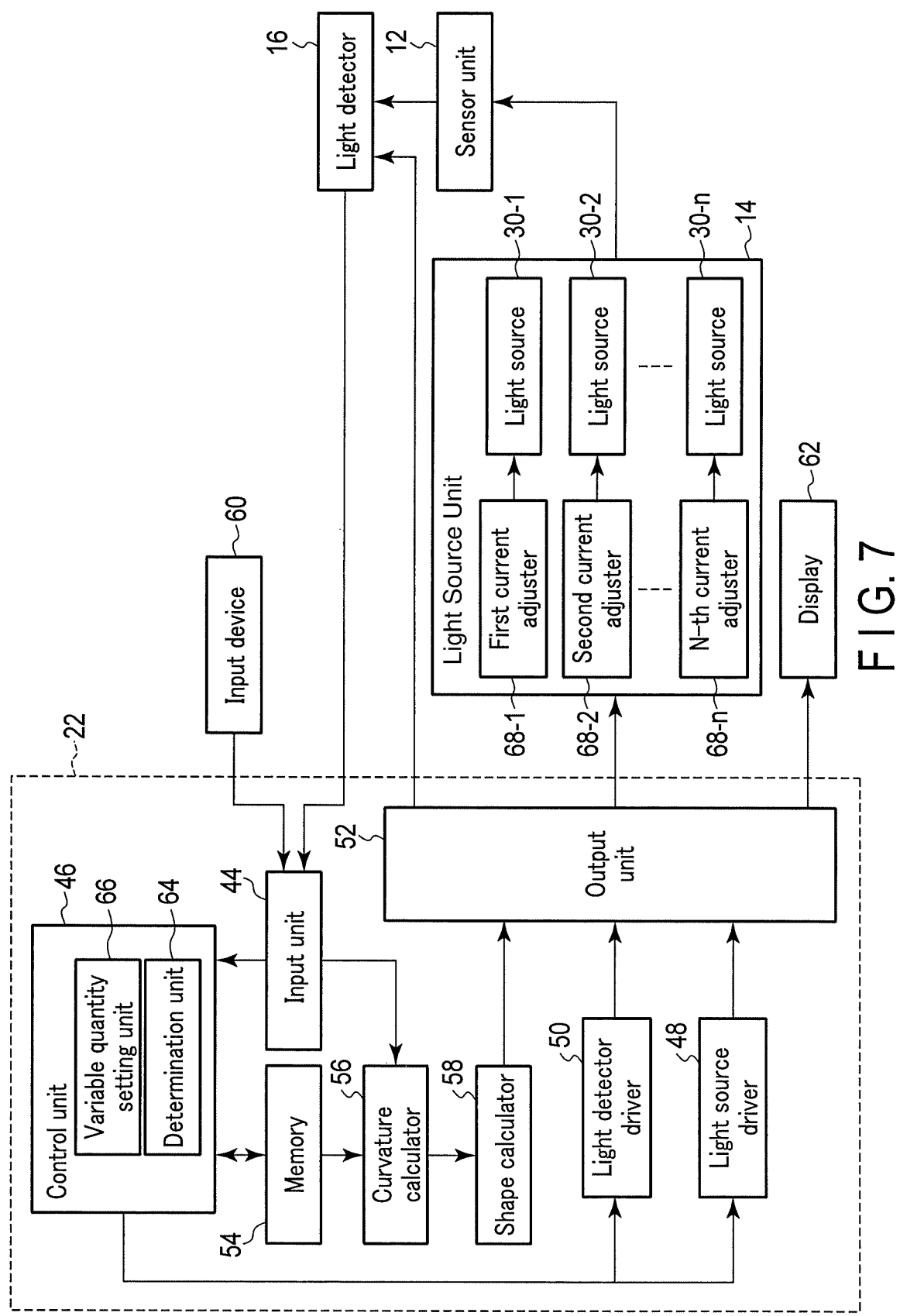
FIG. 7 is a block diagram showing a functional configuration of a processor and its peripheral parts of the shape calculating apparatus according to the first embodiment.

The processor 22, as shown in FIG. 7, comprises an input unit 44, a control unit 46, a light source driver 48, a light detector driver 50, an output unit 52, a memory 54, a curvature calculator 56, and a shape calculator 58. The processor 22 is constituted by, for example, a computer.

The input unit 44 receives input data given from the outside of the processor 22, and provides it for the control unit 46 and the curvature calculator 56 as necessary. Specifically, to the input unit 44, a detection signal of the sensor unit 12 that is digitalized by an AD converter (not illustrated) from the light detector 16 is input. Furthermore, an exposure end signal is also input from the light detector 16 to the input unit 44. In addition, to the input unit 44, a curvature computation start signal, a curvature computation end signal, sensor identification information, a signal concerning the setting of the curvature calculator 56, etc. are input from an input device 60. The input device 60 contains a switch or a button for instructing the start/end of curvature computation. The input device 56 also includes a keyboard for choosing a type of the sensor unit 12 or setting the curvature calculator 56 by inputting information with respect to the menu or options displayed on a display 62. The input device 56 can further include communication equipment by which information is externally input through a wireless or wired network can be included.

The control unit 46 performs the function of improving the resolution of light quantity information by changing the dynamic range of the intensity of light input to the sensor unit 12. This control unit 46 comprises a determination unit 64 and a variable quantity setting unit 66. The determination unit 64 determines the state in magnitude of the detection signal of the light detector 16, when the input unit 44 obtains the exposure end signal from the light detector 16. Specifically, the determination unit 64 determines whether or not a piece of light quantity information of each wavelength from the light detector 16 is within the range of the threshold of the lower detection limit (lower limit threshold) and the threshold of the upper detection limit (upper limit threshold), and determines a change of the dynamic range when a piece of light quantity information is outside the range of the thresholds. At the time of the change of the dynamic range, the variable quantity setting unit 66 is changed so as to change the light quantity of a light source close to a wavelength range outside the range of the thresholds, of the first light source 30-1, the second light source 30-2, . . . , and the n-th light source 30-n, and return the light quantity information of the light detector 16 within the range between the upper limit threshold and the lower limit threshold. The variable quantity setting unit 66 changes the setting of the light intensity of each light source 30 of the light source unit 14 through the light source driver 48.

The upper limit threshold and the lower limit threshold to be used by the determination unit 64 are previously stored in the memory 54. It is also possible to input the upper limit threshold and the lower limit threshold from the input device 60, and store them in the memory 54. That is, the input device 60 can be used as an instruction unit that instructs a change of information relating to a determination in the determination unit 64.

The light source unit 14 comprises n current adjusters 68 (the first current adjuster 68-1, the second current adjuster 68-2, . . . , the n-th current adjuster 68-n) each of which changes the intensity of light emitted from each of the n light sources 30. The light source driver 48 transmits information on light intensity set by the variable quantity setting unit 66 to each current adjuster 68 of the light source unit 14 through the output unit 52. Each current adjuster 68 can adjust the intensity of light input to the sensor unit 12 by driving the first light source 30-1, the second light source 30-2, . . . , and the n-th light source 30-n of an LD, etc. with driving currents according to the information on light intensity from the light source driver 48.

The control unit 46 controls the operations of the light detector 16 through the light detector driver 50. Specifically, when the input unit 44 receives a curvature computation start signal from the input device 60, the variable quantity setting unit 66 of the control unit 46 performs the initial setting of an exposure time and sensitivity of the light detector 16 through the light detector driver 50. Thereby, the light detector 16 detects the detection signal component of each wavelength from the sensor unit 12 by the exposure time and sensitivity of the initial setting.

The memory 54 previously stores curvature characteristic information according to various types of settings of the light detector 16 and the light source unit 14, for each type of the available sensor unit 12.

The curvature calculator 56, based on the detection signal from the input unit 44, and curvature characteristic information according to various types of settings of the light detector 16 and each light source 30 of the light source unit 14 stored in the memory 54 that corresponds to sensor identification information to be input to the input unit 44 from the input device 60, calculates curvature information on each detection target 26 (the first detection target 26-1, the second detection target 26-2, . . . , and the n-th detection target 26-n) of the sensor unit 12. The curvature calculator 56 transmits the calculated curvature information on each detection target 26 to the shape calculator 58.

The shape calculator 58 converts the curvature information on each detection target 26 to shape information on the structure of the insertion section, etc. of the endoscope. The shape calculator 58 transmits the shape information on the structure to the display 62 through the output unit 52.

The display 62 displays the shape information on the structure.

Figure 8:
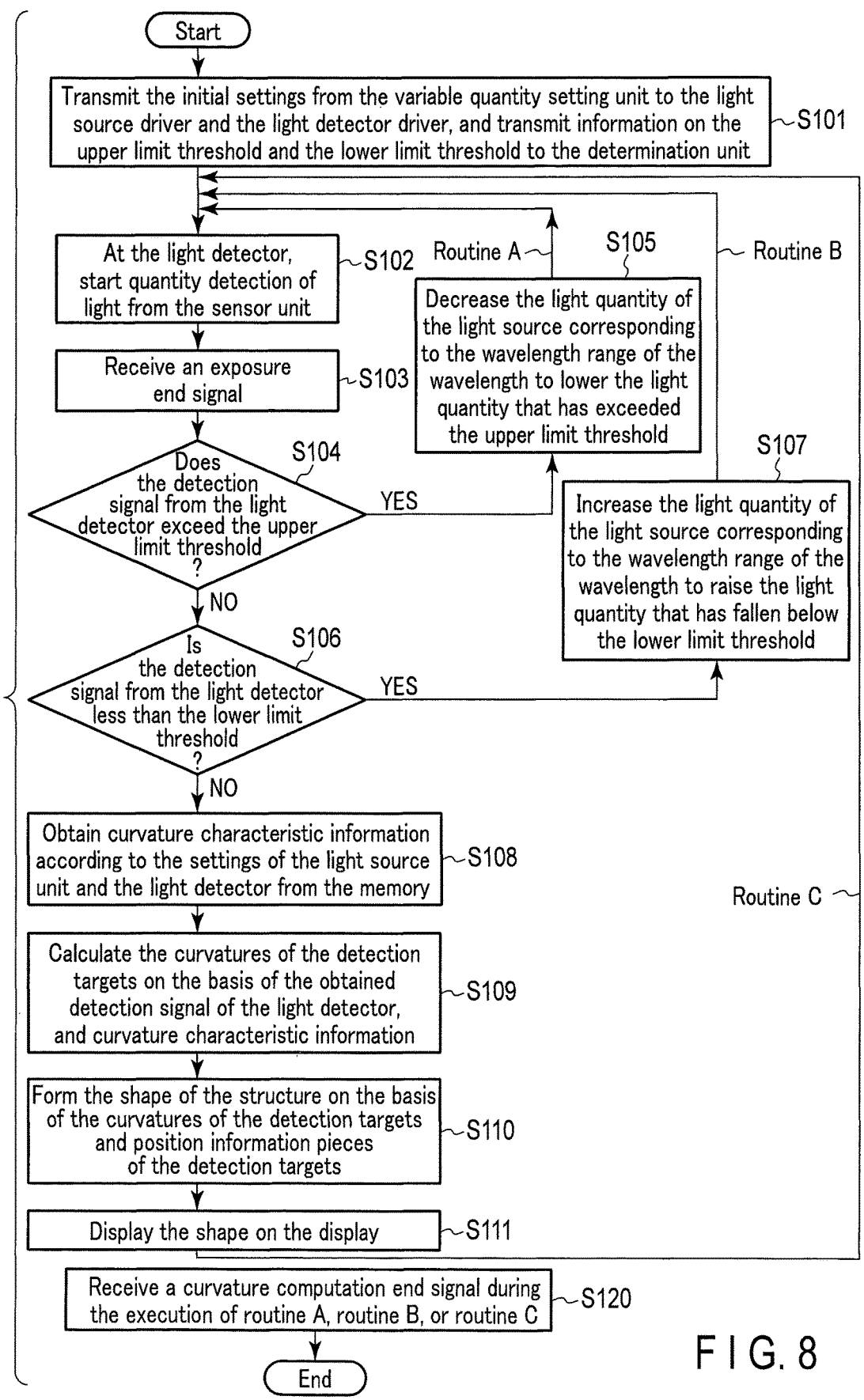
FIG. 8 is an operational flowchart of the shape calculating apparatus according to the first embodiment.

Hereinafter the operations of the processor 22 of the shape calculating apparatus 10 according to the first embodiment will be further described with reference to the flowchart of FIG. 8.

If the input unit 44 receives a curvature computation start signal from the input device 60, the operations of this flowchart are started. First, the control unit 46 transmits the initial settings from the variable quantity setting unit 66 to the light source driver 48 and the light detector driver 50, and reads information on the upper limit threshold and the lower limit threshold from the memory 54 and transmits it to the determination unit 64 (step S101). According to the initial settings from the variable quantity setting unit 66, the light source driver 48 and the light detector driver 50 change the settings of the light source driver 48 and the light detector driver 50, and transmit the information on the changed settings to the light source unit 14 and the light detector 16 through the output unit 52. Thereby, the light intensity of each light source 30 of the light source unit 14 and the exposure time and sensitivity of the light detector 16 are initialized.

By such initial settings, the emission of light from the light source unit 14 is started, and the light detector 16 starts detecting the quantity of light of each wavelength from the sensor unit 12 (step S102). The information on the detected light quantity is input to the input unit 44, and stored in a memory (not illustrated) constituted in the input unit 44, or in the memory 54.

The light detector 16, upon completing light quantity detection for all the wavelengths, outputs an exposure end signal. If the input unit 44 receives the exposure end signal from the light detector 16 (step S103), the determination unit 64 of the control unit 46 determines whether or not the detection signal from the light detector 16, which varies along with the shape change of the light guide 24 of the sensor unit 12, which bends by following the bend state of the structure, exceeds the upper limit threshold (step S104). It is desirable that the upper limit threshold is slightly lower than the measurement limit of the light detector 16.

Figure 9A:
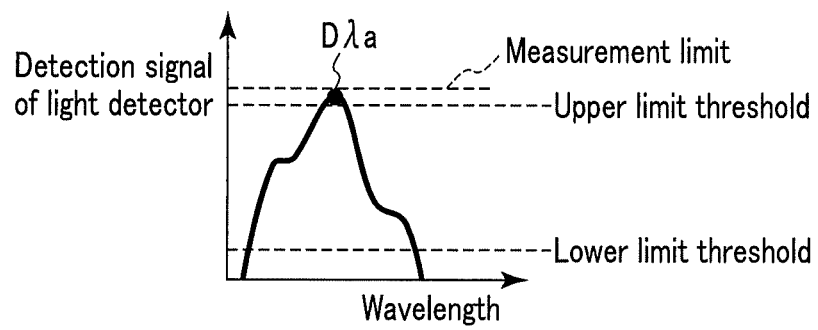
FIG. 9A is a view showing a detection signal of a light detector before a change of variable quantity setting when the detection signal has exceeded an upper limit threshold.

For example, if a piece of light quantity information to be used for curvature calculation has exceeded the upper limit threshold (e.g., light quantity information Dλa), that is, when, of the detection signal of the light detector 16, any of the light intensities of the wavelengths to be used for curvature calculation has exceeded the upper limit threshold, as shown in FIG. 9A, the determination unit 64 outputs the information indicative of it to the variable quantity setting unit 66.

Figure 9B:
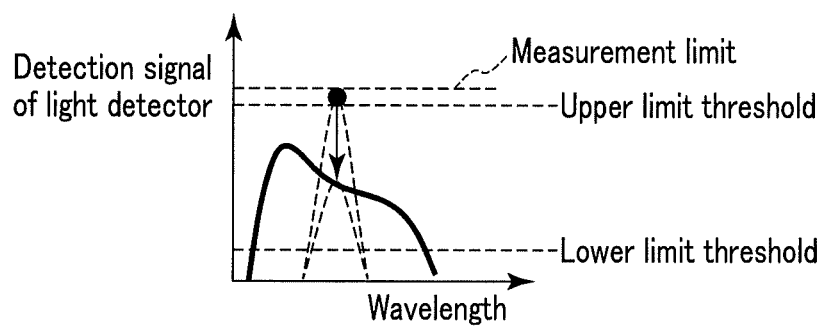
FIG. 9B is a view showing a detection signal of the light detector after the change of the variable quantity setting when the detection signal has exceeded the upper limit threshold.

After receiving the information indicating that at least a piece of light quantity information to be used for curvature calculation has exceeded the upper limit threshold, the variable quantity setting unit 66, to lower the detection signal component of the wavelength that has exceeded the upper limit threshold, makes the setting change of decreasing the light quantity of the light source 30 corresponding to the wavelength range of the wavelength, as shown in FIG. 9B (step S105). That is, the variable quantity setting unit 66 transmits to the light source driver 48 the setting information for changing the setting of the current adjuster 68 corresponding to the light source 30 of the wavelength range of the wavelength at which the light quantity has exceeded the upper limit threshold, of the n current adjusters 68 of the light source unit 14, to lower the detection signal of the light detector 16. The operations return to the processing in step S102.

In such a manner, a routine A composed of step S102, step S103, step S104, and step S105 can be repeated. That is, when a wavelength at which the detection signal exceeds the upper limit threshold still exists even after a setting change, to further lower the detection signal component of the light detector 16 of the wavelength, the setting of the corresponding current adjuster 68 of the light source unit 14 is changed through the light source driver 48. As described above, the setting of each current adjuster 68 of the light source unit 14 can be changed as necessary so as to obtain the detection signal of the light detector 16 in the optimum setting.

On the other hand, in step S104, if the determination unit 64 determines that the detection signal from the light detector 16 does not exceed the upper limit threshold, the determination unit 64 further determines whether or not the detection signal of the light detector 16 is less than the lower limit threshold (step S106).

Figure 10A:
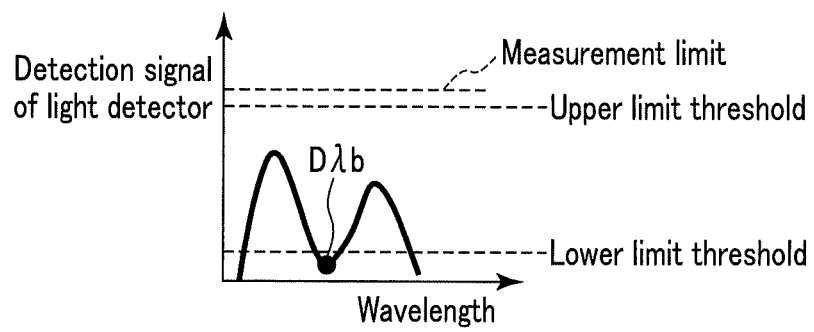
FIG. 10A is a view showing a detection signal of the light detector before a change of variable quantity setting when the detection signal has fallen below a lower limit threshold.
Figure 10B:
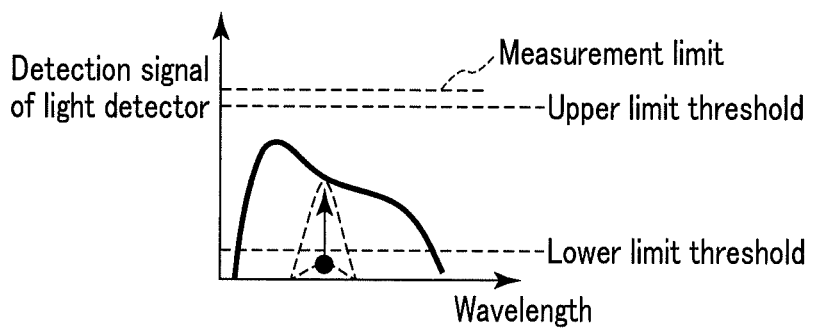
FIG. 10B is a view showing a detection signal of the light detector after the change of the variable quantity setting when the detection signal has fallen below the lower limit threshold.

For example, if a piece of light quantity information to be used for curvature calculation has fallen below the lower limit threshold (e.g., light quantity information Dλb) as shown in FIG. 10A, the determination unit 64 outputs the information indicative of such to the variable quantity setting unit 66. Upon receiving this, the variable quantity setting unit 66, to raise the detection signal component of the wavelength that has fallen below the upper limit threshold, makes the setting change of increasing the light quantity of the light source 30 corresponding to the wavelength range of the wavelength, as shown in FIG. 10B (step S107). That is, the variable quantity setting unit 66 transmits to the light source driver 48 the setting information for changing the setting of the current adjuster 68 corresponding to the light source 30 of the wavelength range of the wavelength at which the light quantity has fallen below the lower limit threshold, of the n current adjusters 68 of the light source unit 14, to raise the detection signal of the light detector 16. Thereby, when the detection signal of the light detector 16 has fallen below the lower limit threshold as a result of the setting change of lowering the detection signal of the light detector 16 in step S105, for example, the setting of the light source unit 14 can be changed to return to the preceding stage. The operations return to the processing in step S102.

In such a manner, a routine B composed of step S102, step S103, step S104, step S106, and step S107 can be repeated. That is, when a wavelength at which the detection signal is less than the lower limit threshold still exists even after a setting change, to further raise the detection signal component of the wavelength of the light detector 16, the setting of the corresponding current adjuster 68 of the light source unit 14 is changed through the light source driver 48. As described above, the setting of each current adjuster 68 of the light source unit 14 can be changed as necessary so as to obtain the detection signal of the light detector 16 in the optimum setting.

If the determination unit 64 determines that the detection signal from the light detector 16 does not exceed the upper limit threshold in step S104, and determines that the detection signal from the light detector 16 does not fall below the lower limit threshold in step S106, the curvature calculator 56 obtains curvature characteristic information according to the settings of the light source unit 14 and the light detector 16 from the memory 54 (step S108). That is, the curvature calculator 56 obtains from the memory 54 curvature characteristic information based on setting information on each current adjuster 68 of the light source unit 14 from the variable quantity setting unit 66 of the control unit 46, and setting information on the exposure time and sensitivity of the light detector 16. The curvature calculator 56 calculates the curvature of each detection target 26 on the basis of the obtained detection signal of the light detector 16 and this curvature characteristic information (step S109).

The shape calculator 58 forms the shape of the structure on the basis of the curvatures of the detection targets 26 that have been calculated in the curvature calculator 56 and position information pieces of the detection targets 26 that are foresight information (step S110). The shape calculator 58 displays the formed shape of the structure on the display 62 through the output unit 52 (step S111).

After that, the operations from step S101 are repeated.

In such a manner, a routine C composed of step S102 to step S111 is repeated. Thereby, the updated shape of the structure according to the displacement of the structure can be displayed on the display 62.

If the input unit 44 receives a curvature computation end signal from the input device 60 during the execution of the routine A, routine B, or routine C (step S120), the processing in this flowchart is terminated.

Figure 11:
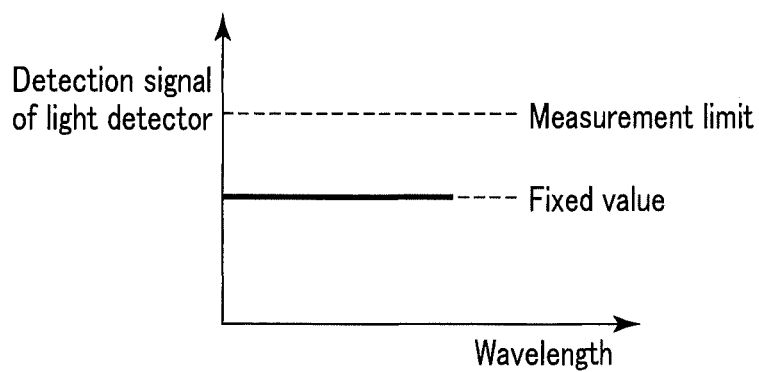
FIG. 11 is a view showing a detection signal of the light detector after changing the variable quantity setting so that the detection signal becomes a fixed value.

The light quantity of the light source 30 is adjusted corresponding to the wavelength range in which a detection signal component from the light detector 16 has exceeded the range of the thresholds, whereby the light quantity is controlled within the range of the thresholds. However, it is also possible to adjust the light intensity of each of the light sources 30-1, 30-2, . . . , and 30-n of the light source unit 14 so that the detection signal from the light detector 16 always becomes a fixed value in regards to the entire wavelength region to be used for shape estimation, without providing any threshold, as shown in FIG. 11.

As described above, the shape calculating apparatus 10 according to the first embodiment comprises the light detector 16 that detects the light quantity information indicating the relationship between the wavelengths and light quantities obtained by the sensor unit 12 configured to sense light quantity relating to a wavelength according to each of the detection targets 26 that differs according to the shape of each of the detection targets 26, the curvature calculator 56 that makes a calculation relating to the shape of each of the detection targets 26 on the basis of the light quantity information, and the control unit (function of improving resolution for each wavelength range) 46 that changes the dynamic range of the intensity of light input to the sensor unit 12 for each predetermined wavelength range.

The shape calculating apparatus 10 as described above can obtain light quantity information indicating the relationship between the wavelengths and light quantities with a high degree of accuracy from the sensor unit 12 including the detection targets 26 by changing the dynamic range of the intensity of light input to the sensor unit 12 for each wavelength range. It thus becomes possible to accurately calculate the shape of each detection target 26.

Here, the shape calculating apparatus 10 further comprises the light sources 30-1, 30-2, . . . , and 30-n, the light intensity of light emitted from each of which is independently changeable, and the control unit 46 changes the light intensity of each of the light sources 30-1, 30-2, . . . , and 30-n, thereby changing the dynamic range of the intensity of light input to the sensor unit 12.

The light sources 30-1, 30-2, . . . , and 30-n differ from one another in optical frequency spectrum. For example, the light sources 30-1, 30-2, . . . , and 30-n can include at least one laser light source different in optical frequency spectrum from the other light sources. Alternatively, even if the light sources 30-1, 30-2, . . . , and 30-n are the same in optical frequency spectrum, they may include intensity changing units that change the intensity of light quantity for each wavelength range. These intensity changing units are disposed on the optical paths from the light sources 30-1, 30-2, . . . , and 30-n to the sensor unit 12. As the intensity changing units, the optical filters 34-1, 34-2, . . . , and 34-n can be used. In this case, the absorbance of the optical filters 34-1, 34-2, . . . , and 34-n can be the same as that used for the detection targets 26-1, 26-2, . . . , and 26-n of the sensor unit 12.

The light sources 30-1, 30-2, . . . , and 30-n or the intensity changing units are different in optical frequency spectrum so that the entire wavelength region used for shape estimation can be covered.

The light sources 30-1, 30-2, . . . , and 30-n or the intensity changing units are different in optical frequency spectrum so that the light intensities of the frequencies of light used for shape estimation can be sufficiently changed.

The control unit 46 changes the dynamic range of the intensity of light input to the sensor unit 12 by changing the light intensity of each of the light sources 30-1, 30-2, . . . , and 30-n when a measurement result of the light detector 16 has exceeded the upper limit threshold, or has fallen below the lower limit threshold.

The control unit 46 changes the dynamic range of the intensity of light input to the sensor unit 12 by changing the light intensity of each of the light sources 30-1, 30-2, . . . , and 30-n so that a measurement result of the light detector 16 can be fixed.

The shape calculating apparatus 10 can further comprise the light source unit 14 containing the light sources 30-1, 30-2, . . . , and 30-n that emit light and the sensor unit 12.

Here, the sensor unit 12 contains the light guide 24 that is a light guiding member that guides light emitted from the light source unit 14, and the detection targets 26 respectively including the detection target materials 42 that are constituted by optical characteristic changing materials provided in the light guide 24 and exert influences different from one another on the spectrum of light guided by the light guide 24. The light detector 16 detects light that is guided by the light guide 24 and influenced by the detection target materials 42, and outputs light quantity information.

Second Embodiment

Next, the second embodiment of the present invention will be described. Here, the differences from the first embodiment previously discussed will be described, and the descriptions of the same portions will be omitted by the addition of the same codes.

The shape calculating apparatus 10 according to the first embodiment shows an example of changing the dynamic range of the intensity of light input to the sensor unit 12. On the other hand, the shape calculating apparatus 10 according to the present second embodiment shows an example of changing, for each wavelength range, the dynamic range of a detection signal of the light detector 16 that is an electrical signal generated by the light detector 16 on the basis of light output from the sensor unit 12.

Figure 12:
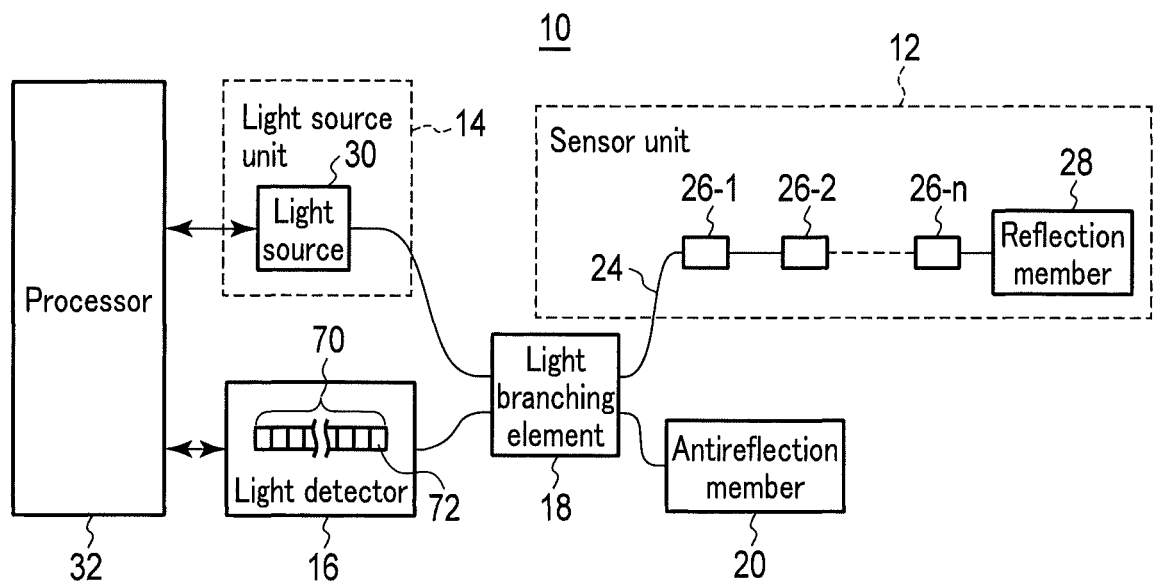
FIG. 12 is a view showing a schematic configuration of a shape calculating apparatus according to a second embodiment of the present invention.

Thus, in the shape calculating apparatus 10 according to the present embodiment, the light source unit 14 contains only one light source 30 as shown in FIG. 12. In addition, the light detector 16 includes a line sensor 70 constituted by pixel sensors 72. Each pixel sensor 72 of the line sensor 70 measures the light intensities of the wavelength ranges different from one another.

Figure 13:
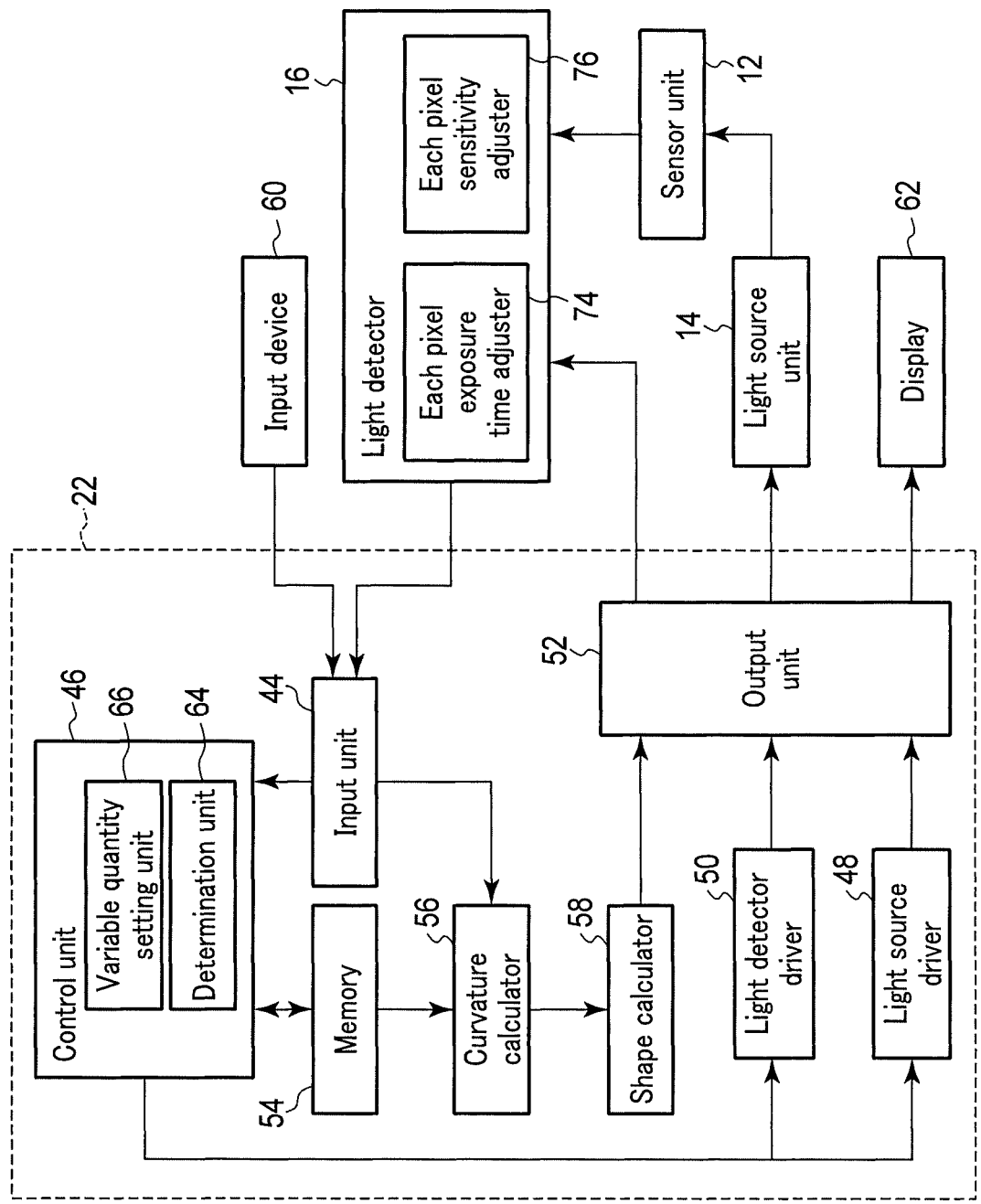
FIG. 13 is a block diagram showing a functional configuration of a processor and its peripheral parts of the shape calculating apparatus according to the second embodiment.

The light detector 16 comprises an each pixel exposure time adjuster 74 that changes the exposure time of each pixel sensor 72, as shown in FIG. 13. Alternatively, the light detector 16 can comprise an each pixel sensitivity adjuster 76 that changes the sensitivity of each pixel sensor 72 by changing the gain setting of the charge amplifier circuit (not shown) of the light detector 16 according to an output timing of each pixel sensor 72. The control unit 46 of the processor 22 transmits to the each pixel exposure time adjuster 74 or the pixel sensitivity adjuster 76 through the light detector driver 50 and the output unit 52 the setting information on, for example, a change of the exposure time or sensitivity of the pixel sensor 72 corresponding to the wavelength range in which a detection signal component from the light detector 16 has exceeded the range of the thresholds. The shape calculating apparatus 10 according to the present second embodiment changes the dynamic range of the detection signal of the light detector 16 for each wavelength range by changing the exposure time or sensitivity of each pixel sensor 72 in such a manner.

Figure 14:
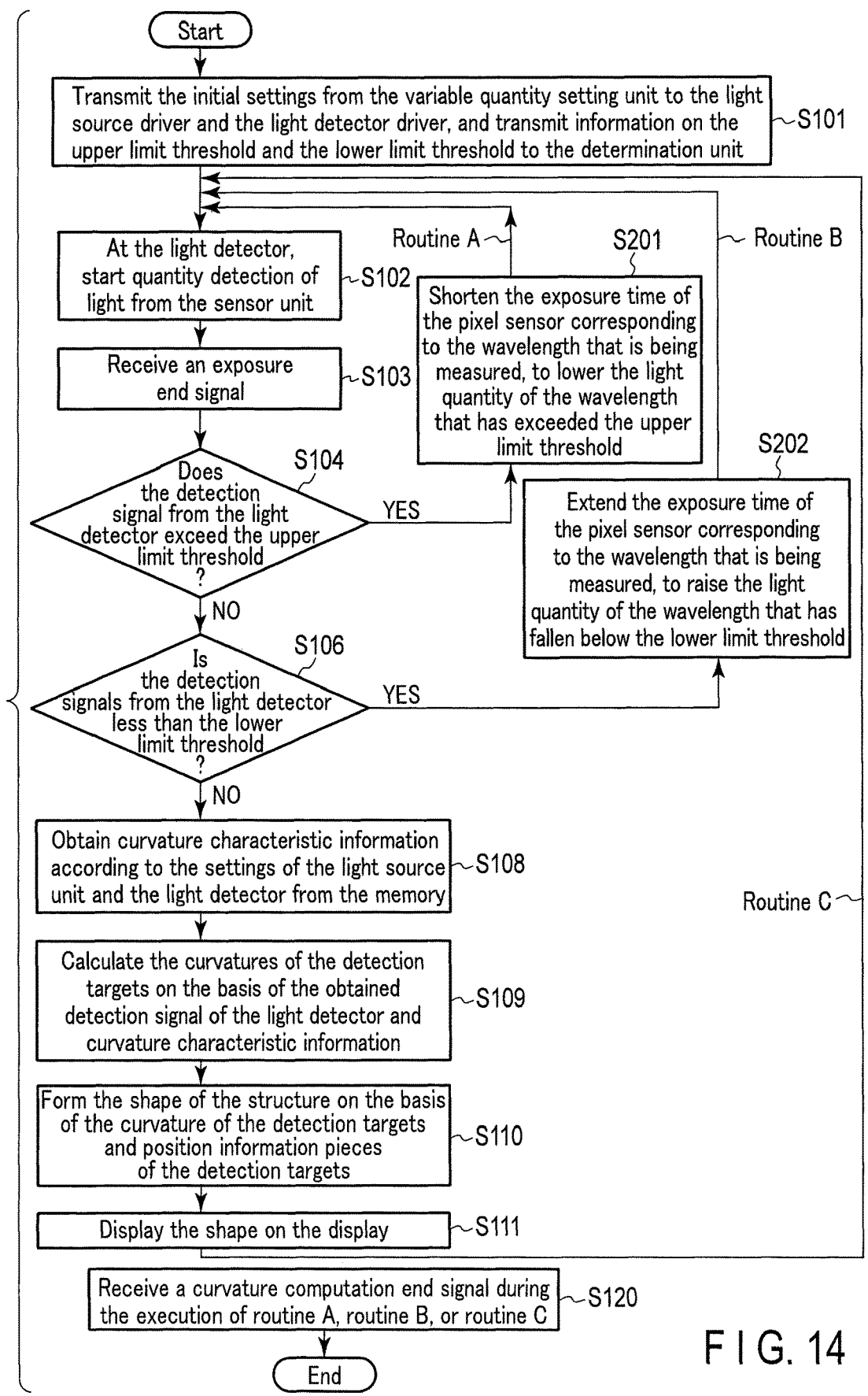
FIG. 14 is an operational flowchart of the shape calculating apparatus according to the second embodiment.

Hereinafter the operations of the processor 22 of the shape calculating apparatus 10 according to the present second embodiment will described with reference to the flowchart of FIG. 14.

If the input unit 44 receives a curvature computation start signal from the input device 60, the operations of this flowchart are started. The operations shown in this flowchart are basically the same as the first embodiment. Only step S105 in the routine A and step S107 in the routine B in the first embodiment are replaced with step S201 and step S202, respectively.

Figure 15A:
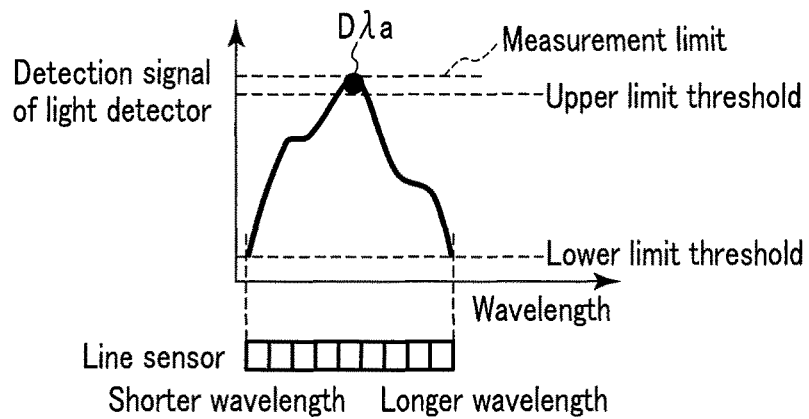
FIG. 15A is a view showing a detection signal of the light detector before a change of variable quantity setting when the detection signal has exceeded an upper limit threshold.

That is, in step S104, if the determination unit 64 of the control unit 46 determines that a piece of light quantity information to be used for curvature calculation has exceeded the upper limit threshold (e.g., light quantity information D$\lambda$a), that is, of the detection signal of the light detector 16, any of the light intensities of the wavelengths to be used for curvature calculation has exceeded the upper limit threshold, as shown in FIG. 15A, for example, the determination unit 64 outputs the information indicative of it to the variable quantity setting unit 66.

Figure 15B:
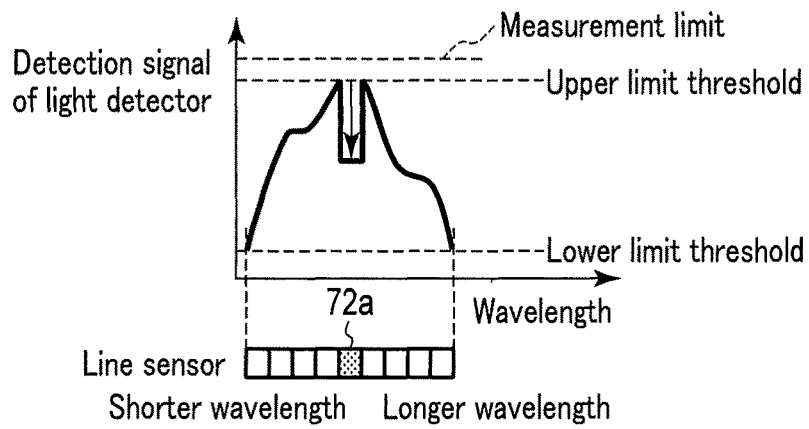
FIG. 15B is a view showing a detection signal of the light detector after the change of the variable quantity setting when the detection signal has exceeded the upper limit threshold.

After receiving the information indicating that at least a piece of light quantity information to be used for curvature calculation has exceeded the upper limit threshold, the variable quantity setting unit 66, to lower the detection signal component of the wavelength that has exceeded the upper limit threshold, makes the setting change of shortening the exposure time of a pixel sensor 72a corresponding to the wavelength range of the wavelength of the pixel sensors 72 of the line sensor 70, as shown in FIG. 15B (step S201). That is, the variable quantity setting unit 66 transmits, to the each pixel exposure time adjuster 74 through the light detector driver 50, the setting information for changing the setting of the exposure time of the pixel sensor 72a that measures light of the wavelength range including the wavelength at which the piece of light quantity information has exceeded the upper limit threshold, of the pixel sensors 72 of the line sensor 70 of the light detector 16, to lower the detection signal component of the pixel sensor 72a. The operations return to the processing in step S102.

In step S201, instead of shortening the exposure time, lowering the sensitivity is also possible. That is, the variable quantity setting unit 66 may transmit to the each pixel sensitivity adjuster 76 through the light detector driver 50 the setting information for changing the setting of the sensitivity of the pixel sensor 72a that measures light of the wavelength range including the wavelength at which the piece of light quantity information has exceeded the upper limit threshold, of the pixel sensors 72 of the line sensor 70 of the light detector 16, to lower the detection signal component of the pixel sensor 72a.

Figure 16A:
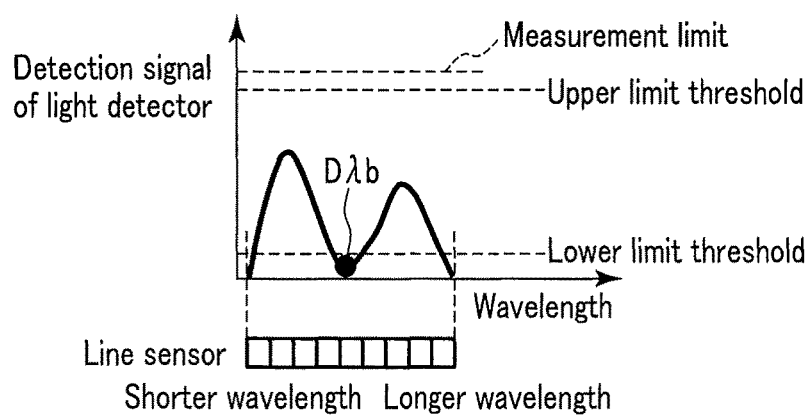
FIG. 16A is a view showing a detection signal of the light detector before a change of variable quantity setting when the detection signal has fallen below a lower limit threshold.

In addition, in step S106, if the determination unit 64 of the control unit 46 determines that a piece of light quantity information to be used for curvature calculation has fallen below the lower limit threshold (e.g., light quantity information D$\lambda$b), that is, of the detection signal of the light detector 16, any of the light intensities of the wavelengths to be used for curvature calculation have fallen below the lower limit threshold, as shown in FIG. 16A, for example, the determination unit 64 outputs the information indicative of it to the variable quantity setting unit 66.

Figure 16B:
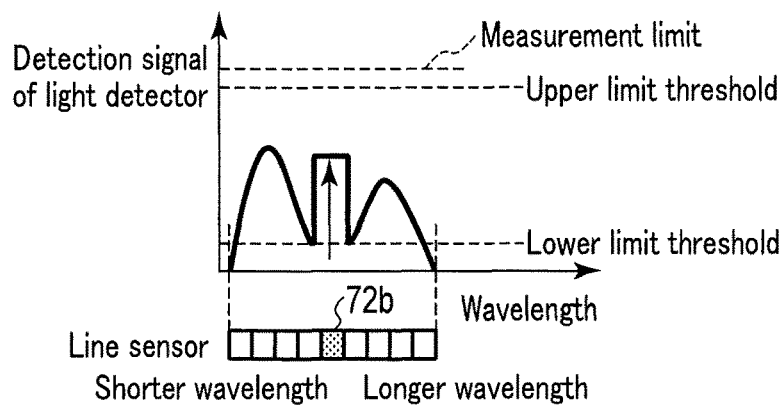
FIG. 16B is a view showing a detection signal of the light detector after the change of the variable quantity setting when the detection signal has fallen below the lower limit threshold.

After receiving the information indicating that at least a piece of light quantity information to be used for curvature calculation has fallen below the lower limit threshold, the variable quantity setting unit 66, to raise the detection signal component of the wavelength that has fallen below the lower limit threshold, makes the setting change of extending the exposure time of a pixel sensor 72b corresponding to the wavelength range of the wavelength of the pixel sensors 72 of the line sensor 70, as shown in FIG. 16B (step S202). That is, the variable quantity setting unit 66 transmits to the each pixel exposure time adjuster 74 through the light detector driver 50 the setting information for changing the setting of the exposure time of the pixel sensor 72b that measures light of the wavelength range including the wavelength at which the piece of light quantity information has fallen below the lower limit threshold, of the pixel sensors 72 of the line sensor 70 of the light detector 16, to raise the detection signal component of the pixel sensor 72b. However, there is the upper limit time of a configurable exposure time for each pixel sensor 72, and the variable quantity setting unit 66 does not make a change for an exposure time equal to or longer than the upper limit time. The operations return to the processing in step S102.

In step S202, instead of extending the exposure time, raising the sensitivity is also possible. That is, the variable quantity setting unit 66 may transmit to the each pixel sensitivity adjuster 76 through the light detector driver 50 the setting information for changing the setting of the sensitivity of the pixel sensor 72b that measures light of the wavelength range including the wavelength at which the piece of light quantity information has fallen below the lower limit threshold, of the pixel sensors 72 of the line sensor 70 of the light detector 16, to raise the detection signal component of the pixel sensor 72b.

Figure 16C:
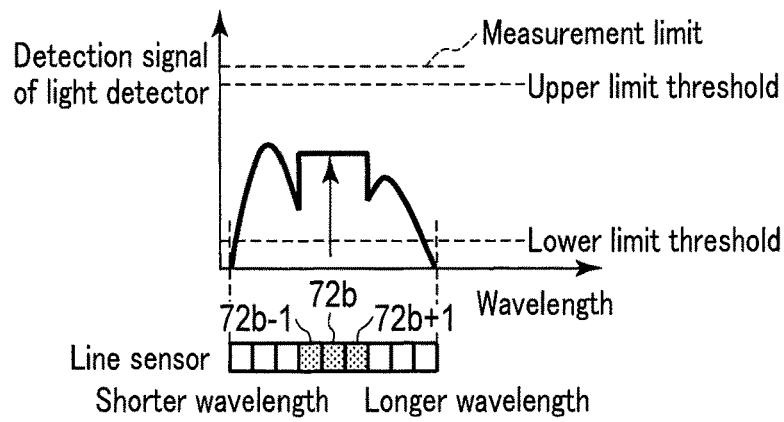
FIG. 16C is a view showing another example of the detection signal of the light detector after the change of the variable quantity setting when the detection signal has fallen below the lower limit threshold.

In addition, in step S202, a change of an exposure time or sensitivity may be made for not only the pixel sensor 72b that measures light of the wavelength range including the wavelength at which the piece of light quantity information has fallen below the lower limit threshold, but also pixel sensors 72b−1 and 72b+1 that measure light of the wavelength ranges adjacent to the aforementioned wavelength range as shown in FIG. 16C. That is, since the wavelength ranges adjacent to the wavelength range including the wavelength at which the piece of light quantity information has fallen below the lower limit threshold do not reach the lower limit threshold but are close to the lower limit threshold, it is desirable to change the exposure time or sensitivity of each of the pixel sensors that measure light of the adjacent wavelength ranges as well in the same manner. The same is true of a change of the exposure time or sensitivity of a pixel sensor when the piece of light quantity information has exceeded the upper limit threshold in step S201. Such a change is more effective in step S202 than step S201, since the lower the level of light quantity information is, the worse the detection accuracy is.

Figure 17:
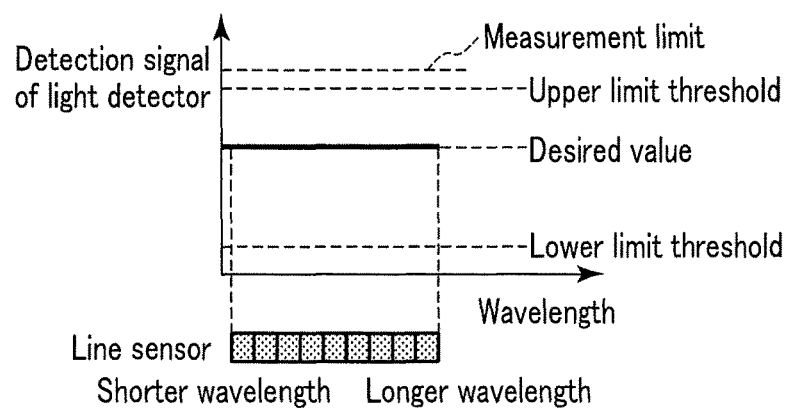
FIG. 17 is a view showing a detection signal of the light detector after changing the variable quantity setting so that the detection signal becomes a desired value.

It is also possible to change all the exposure times or sensitivities of the pixel sensors 72 corresponding to the entire wavelength region to be used for shape estimation in the line sensor 70 so that the detection signal of the light detector 16 comes to be at a fixed desired value as shown in FIG. 17, by the each pixel exposure time adjuster 74 and the each pixel sensitivity adjuster 76.

Figure 18A:
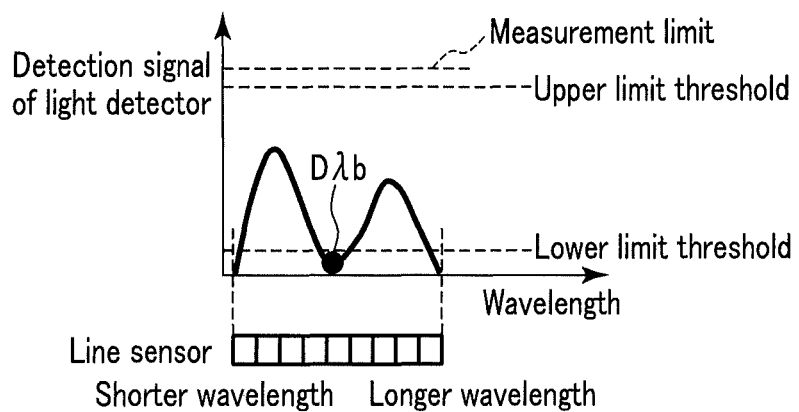
FIG. 18A is a view showing a detection signal of the light detector when a detection signal has fallen below a lower limit threshold.
Figure 18B:
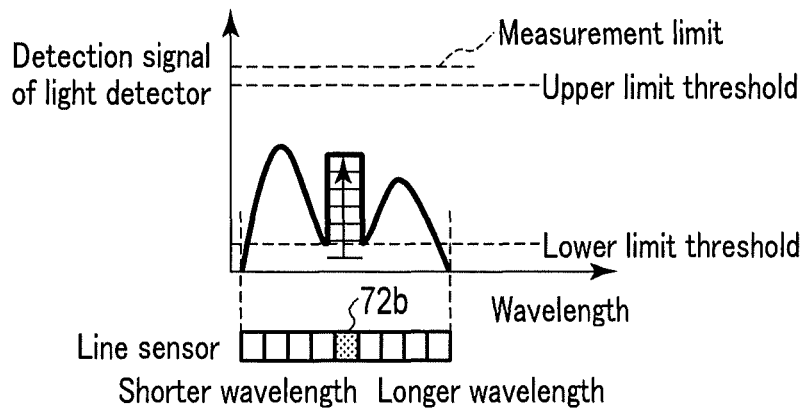
FIG. 18B is a view showing a detection signal of the light detector after a change of variable quantity setting to be used for curvature calculation when a detection signal has fallen below the lower limit threshold.

Alternatively, when a piece of light quantity information (e.g., light quantity information Dλb) has fallen below the lower limit threshold as shown in FIG. 18A, the variable quantity setting unit 66 of the control unit 46, instead of changing the setting of the each pixel exposure time adjuster 74 or the each pixel sensitivity adjuster 76 of the light detector 16, may change the dynamic range of a detection signal of the light detector 16 for each wavelength range by adding up data of the pixel sensor 72b that measures light of the wavelength range in which the piece of light quantity information has fallen below the lower limit threshold multiple times as shown in FIG. 18B. Data will be accumulated by this data addition; however, random noises such as a white noise will be offset.

As described above, the shape calculating apparatus 10 according to the present second embodiment can obtain the light quantity information indicating the relationship between the wavelengths and light quantities with a high degree of accuracy from the sensor unit 12 including the detection targets 26 by changing the dynamic range of the electrical signal generated by the light detector 16 for each wavelength range on the basis of light output from the sensor unit 12. It thus becomes possible to accurately calculate the shape of each detection target 26.

That is, the light detector 16 includes the pixel sensors 72 each of which measures the quantity of light of a wavelength different from others, and the control unit 46 changes the exposure time or sensitivity of each of the pixel sensors 72, thereby changing the dynamic range of an electrical signal that is a detection signal of the light detector 16 for each predetermined wavelength range.

In this case, the control unit 46 changes the exposure time or sensitivity of each pixel sensor 72 so that a measurement result of the light detector 16 can be between the preset upper limit threshold and lower limit threshold. Furthermore, the control unit 46 may change the exposure time or sensitivity of each of not only the pixel sensors 72 corresponding to the wavelength at which the light quantity has exceeded the upper limit threshold or has fallen below the lower limit threshold, but also the pixel sensors 72 corresponding to a wavelength adjacent to the aforementioned wavelength.

Since there is the upper limit time of a configurable exposure time for each pixel sensor 72, the control unit 46 does not make a change in an exposure time equal to or longer than the upper limit time.

Also, the light detector 16 includes the pixel sensors 72 each of which measures the quantity of light of a wavelength different from others, and the control unit 46 may change the number of adding up measurement results for each pixel sensor 72, thereby changing the dynamic range of an electrical signal that is a detection signal of the light detector 16 for each predetermined wavelength range.

The control unit 46 changes the dynamic range of an electrical signal that is a detection signal of the light detector 16 by, when a measurement result of the light detector 16 has exceeded the upper limit threshold or has fallen below the lower limit threshold, changing the exposure time or sensitivity of each of the pixel sensors 72 that measure the quantity of light of the wavelength.

The control unit 46 may change the dynamic range of an electrical signal that is a detection signal of the light detector 16 by changing the exposure time or sensitivity of each of the pixel sensors 72 so that measurement results of the light detector 16 can be fixed.

Third Embodiment

Next, the third embodiment of the present invention will be described. Here, the differences from the first embodiment previously discussed will be described, and the descriptions of the same portions will be omitted by the addition of the same codes.

The shape calculating apparatus 10 according to the present third embodiment, in the same manner as the shape calculating apparatus 10 according to the aforementioned first embodiment, shows an example of changing the dynamic range of the intensity of light input to the sensor unit 12 for each wavelength range.

Figure 19:
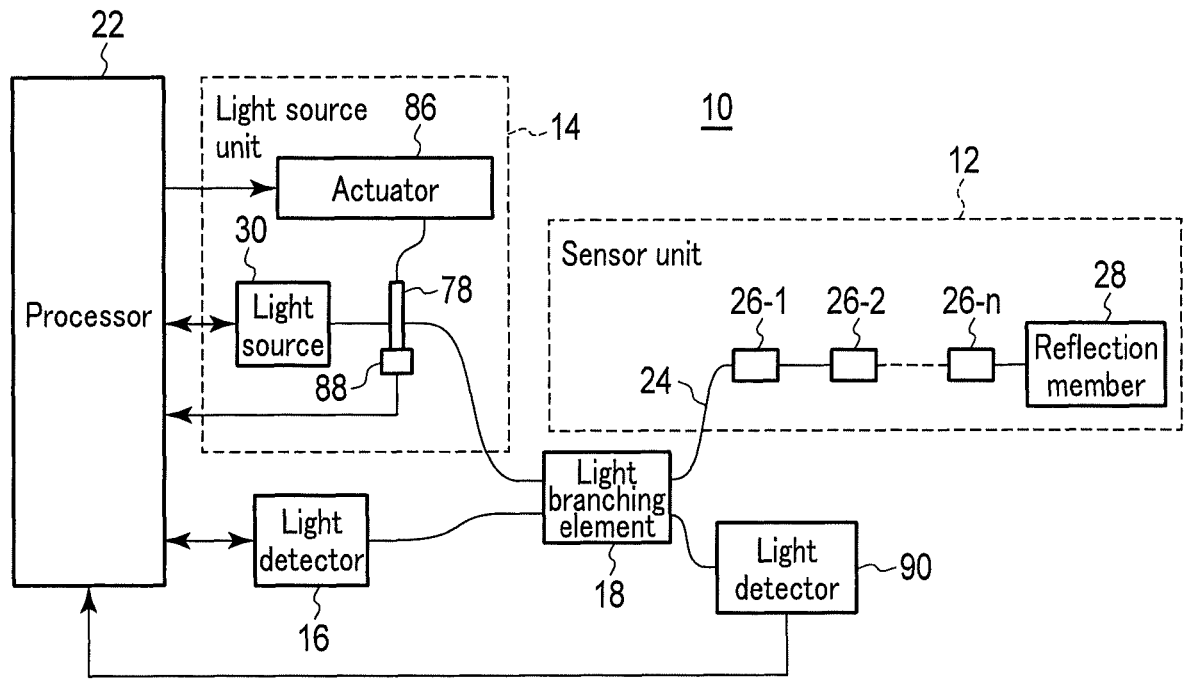
FIG. 19 is a view showing a schematic configuration of a shape calculating apparatus according to a third embodiment of the present invention.

The light source unit 14 includes the light sources 30-1, 30-2, . . . , and 30-n in the first embodiment, but includes only one light source 30 in the present third embodiment as shown in FIG. 19. The light source unit 14 further comprises a movable optical filter 78 mounted with optical filters that transmit light of wavelengths different from one another, between the one light source 30 and the light branching element 18.

Figure 20:
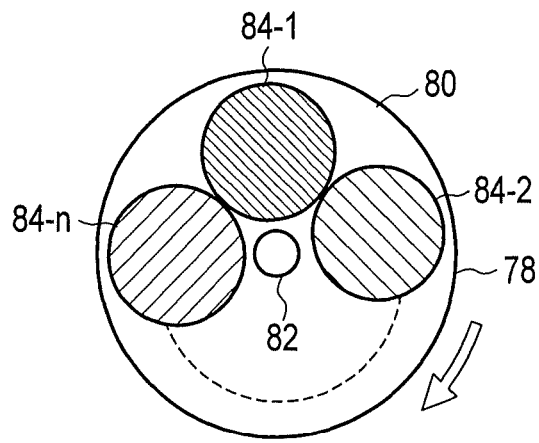
FIG. 20 is a view showing a configuration example of a movable optical filter.

The movable optical filter 78 is a rotary movable optical filter including a rotatable plate 80 that rotates around a rotation axis 82 of a central axis as shown in FIG. 20. In the rotatable plate 80, optical filters 84, the optical absorptivity of each of which differs from the others (the first optical filter 84-1, the second optical filter 84-2, . . . , and the n-th optical filter 84-$n$), are concyclic with respect to the rotation axis 82 as a center. The movable optical filter 78 is disposed in the light source unit 14 so that the rotatable plate 80 rotates around the rotatable axis 82 of a central axis, whereby one of the optical filters 84 is disposed in series on the optical path from the light source 30 to the light branching element 18. Thereby, each optical filter 84 can let only particular wavelengths different from one another of light from one light source 30 pass, and input the light to the sensor unit 12 through the light branching element 18.

Figure 21:
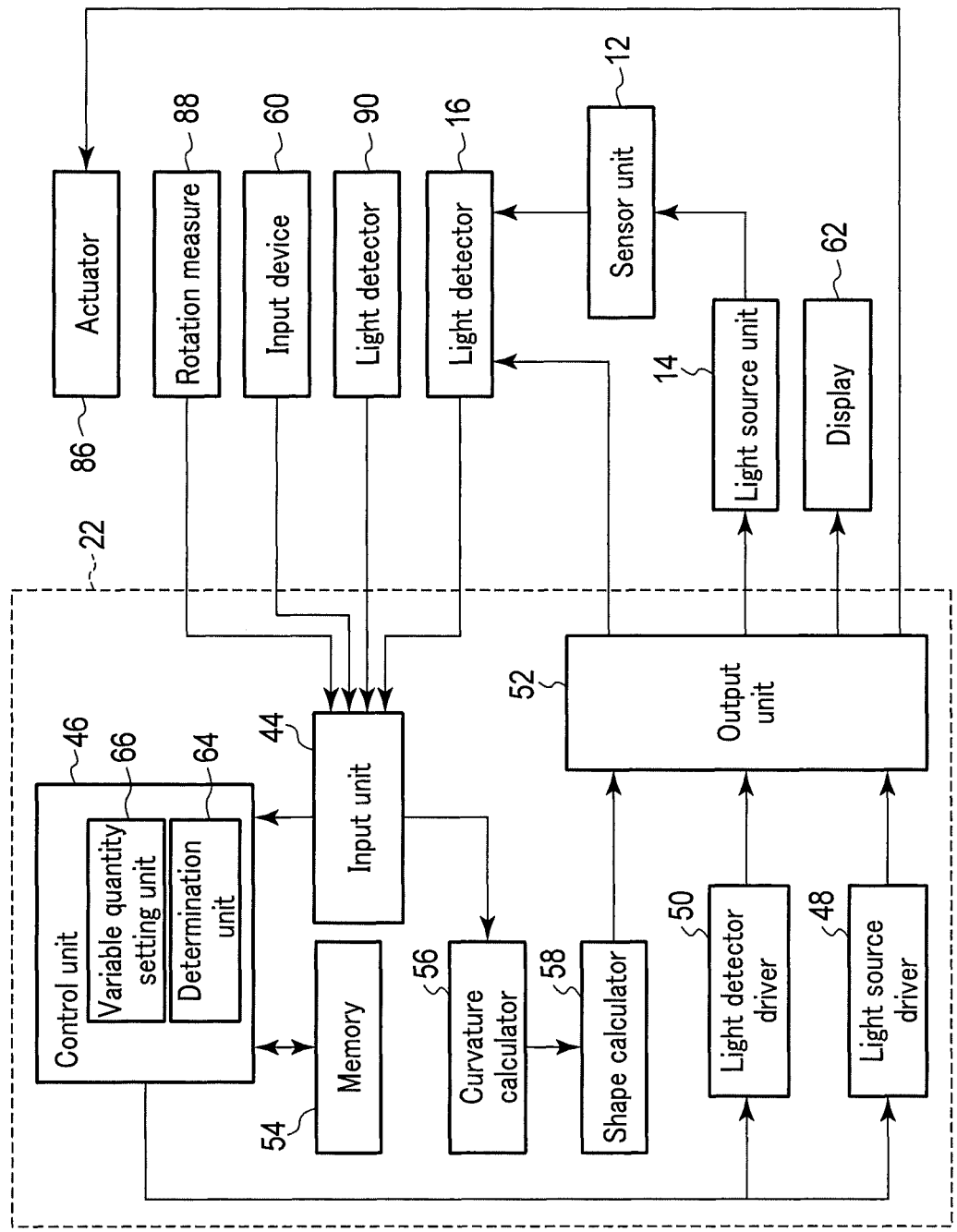
FIG. 21 is a block diagram showing a functional configuration of a processor and its peripheral parts of the shape calculating apparatus according to the third embodiment.

Furthermore, the light source unit 14 includes an actuator 86 for rotating the rotatable plate 80 of the movable optical filter 78, and a rotation measure 88 for measuring the rotation state of the rotatable plate 80 (e.g., pulse encoder). The actuator 86 is controlled by the control unit 46 of the processor 22 through the light source driver 48 and the output unit 52 as shown in FIG. 21. Rotation amount information that is a measurement result of the rotation measure 88 is input to the control unit 46 through the input unit 44 of the processor 22. The control unit 46 can get to know which of the optical filters 84 is disposed on the optical path from the light source 30 to the light branching element 18 on the basis of the rotation amount information from the rotation measure 88. The rotation measure 88 is not restricted to the one that directly detects the rotation amount of the rotatable plate 80, but may be the one that indirectly measures the rotation amount of the rotatable plate 80 with reference to the driving amount, etc. of the actuator 86.

The shape calculating apparatus 10 according to the first embodiment comprises the antireflection member 20 for preventing light that has not entered the light guide 24 from returning to the light detector 16. In contrast, in the shape calculating apparatus 10 according to the present third embodiment, a light detector 90 is provided instead of the antireflection member 20 as shown in FIG. 21. A measurement result of the rotation measure 90 is input to the control unit 46 through the input unit 44 of the processor 22 as shown in FIG. 21. The control unit 46 can confirm the intensity of light that has entered the light guide 24, that is, light input to the sensor unit 12 on the basis of the detection result of the light detector 90. The light detector 90 is not essential.

The variable quantity setting unit 66 of the control unit 46 changes the dynamic range of the intensity of light input to the sensor unit 12 by changing the light intensity of the light source 30 according to the light quantity information from the light detector 16, that is, a detection signal component of each wavelength, so that when the optical path of light from the light source 30 of the light source unit 14 passes through the optical filter 84 that transmits light of wavelengths neighboring the wavelength outside the range of the thresholds, the light quantity outside the range of the thresholds gets back into the range of the thresholds. Alternatively, the dynamic range of the intensity of light input to the sensor unit 12 can be changed, without changing the light intensity of the light source 30, by changing the rotation velocity of the rotatable plate 80 of the movable optical filter 78 by the actuator 86 to change the input time of the light of the wavelength.

The movable optical filter 78 is a rotary movable optical filter in the present embodiment. However, the movable optical filter does not necessarily have to be rotary, of course, as long as it is a movable filter that can achieve desired filter switching.

Figure 22:
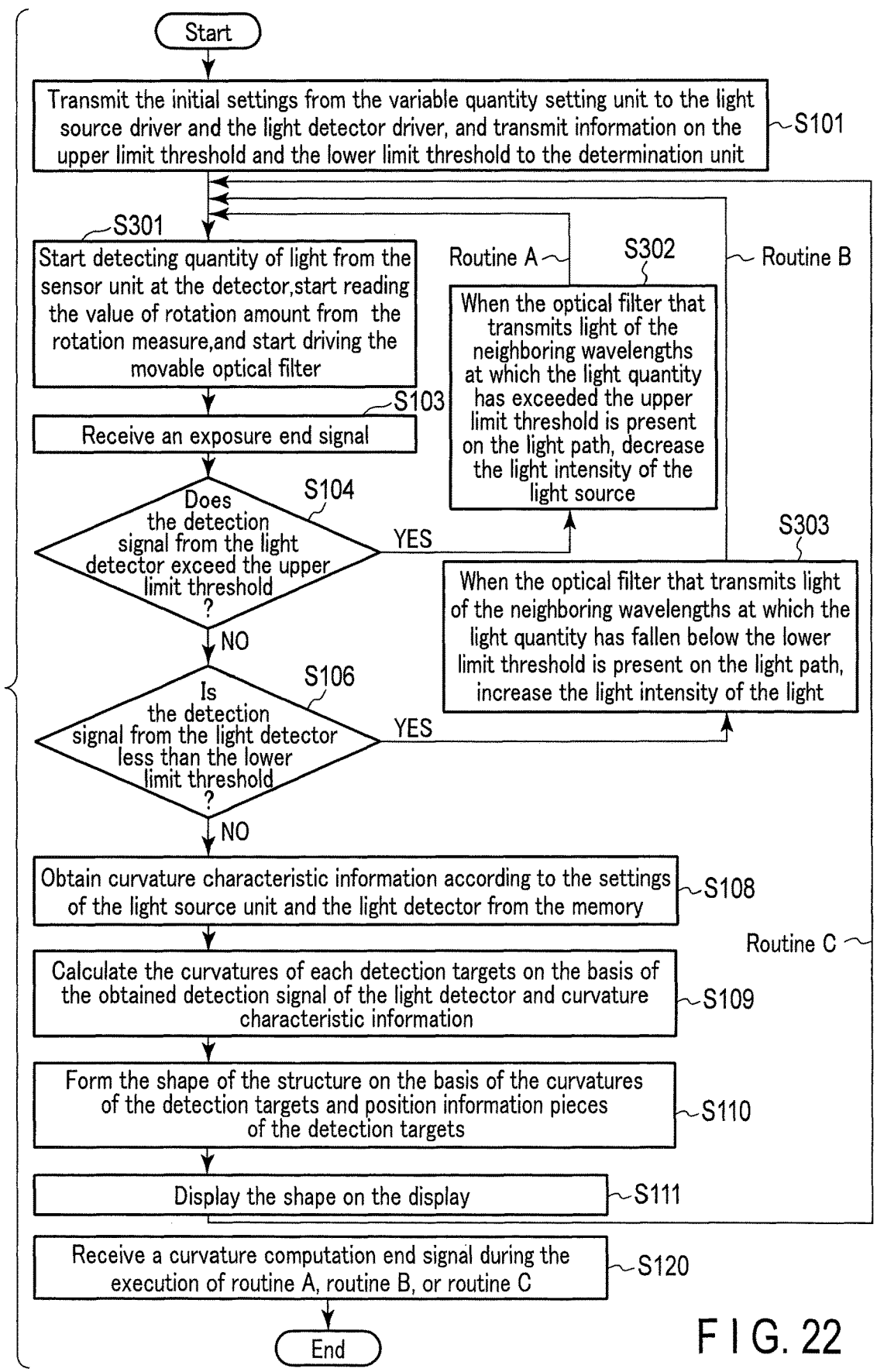
FIG. 22 is a flowchart showing the operations of the shape calculating apparatus according to the third embodiment.

Hereinafter the operations of the processor 22 of the shape calculating apparatus 10 according to the present third embodiment will described with reference to the flowchart of FIG. 22.

If the input unit 44 receives a curvature computation start signal from the input device 60, the operations of this flowchart are started. The operations shown in this flowchart are basically the same as the first embodiment. Only step S102 and step S105 in the routine A and step S107 in the routine B in the first embodiment are replaced with step S301, step S302, and step S303, respectively.

That is, after the initial setting is made in step S101, as in the first embodiment, the control unit 46 has the light source unit 14 start emitting light through the light source driver 48, and the light detector 16 starts quantity detection of light of each wavelength from the sensor unit 12 through the light detector driver 50. Along with this, the control unit 46 starts reading rotation amount information that is the value of rotation amount from the rotation measure 88, and starts driving the movable optical filter 78 by the actuator 86 through the light source driver 48 (step S301). Light quantity information detected by the light detector 16 and rotation amount information measured by the rotation measure 88 are input to the input unit 44, and stored in a memory (not illustrated) configured in the input unit 44, or the memory 54.

Figure 23A:
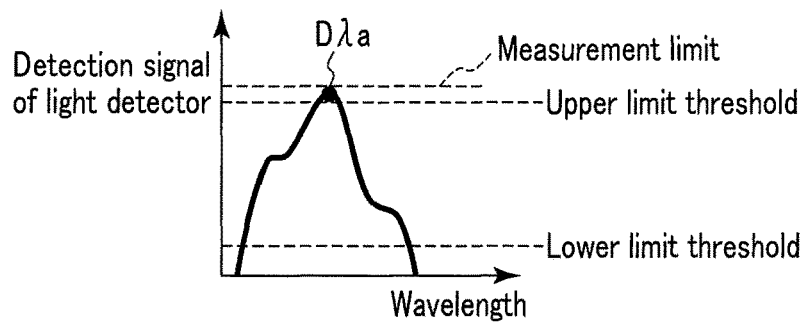
FIG. 23A is a view showing a detection signal of the light detector before a change of variable quantity setting when the detection signal has exceeded an upper limit threshold.

Then, in step S104, if the determination unit 64 of the control unit 46 determines that a piece of light quantity information to be used for curvature calculation has exceeded the upper limit threshold (e.g., light quantity information D$\lambda$a), that is, of the detection signal of the light detector 16, any of the light intensities of the wavelengths to be used for curvature calculation has exceeded the upper limit threshold, as shown in FIG. 23A, for example, the determination unit 64 outputs the information indicative of such to the variable quantity setting unit 66.

Figure 23B:
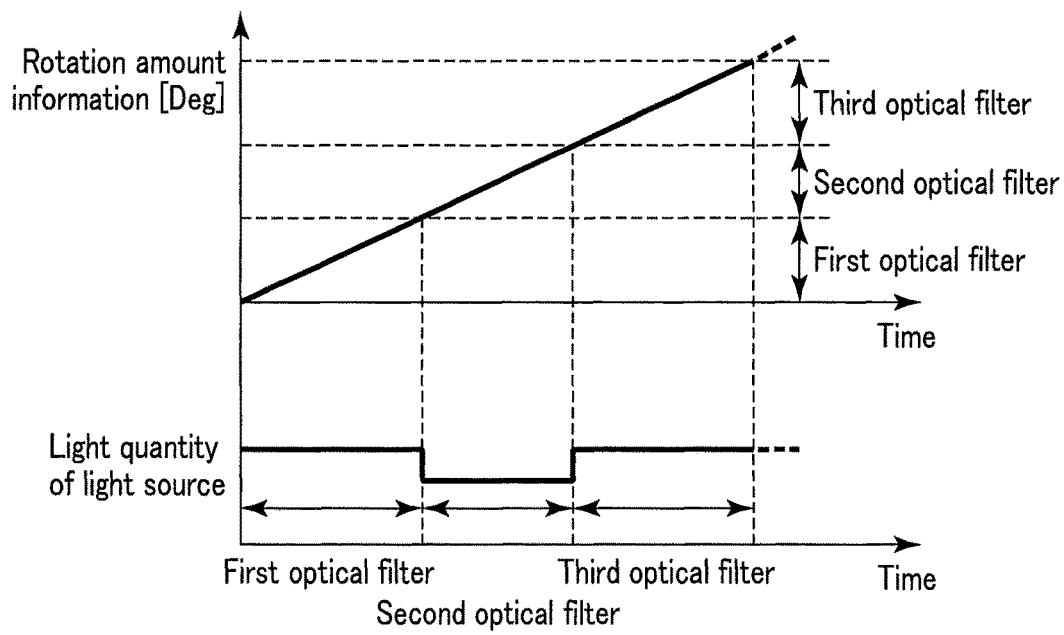
FIG. 23B is a view for describing a method of changing the variable quantity setting by a light intensity change when the detection signal of the light detector has exceeded the upper limit threshold.
Figure 23C:
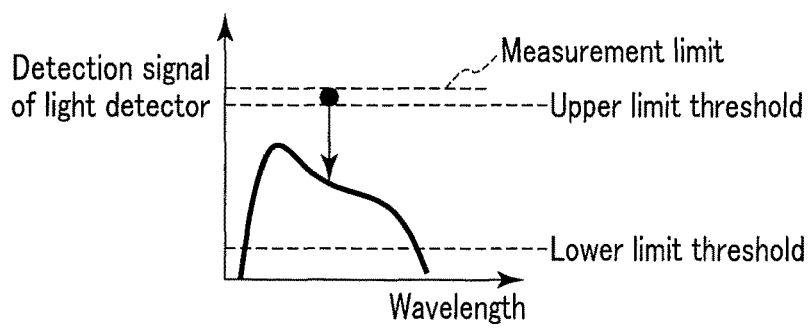
FIG. 23C is a view showing a detection signal of the light detector after the change of the variable quantity setting when the detection signal has exceeded the upper limit threshold.

After receiving the information indicating that at least a piece of light quantity information to be used for curvature calculation has exceeded the upper limit threshold, the variable quantity setting unit 66, as shown in FIG. 23B, makes the setting change of decreasing the light quantity of the light source 30 when the optical filter 84 (e.g., the second optical filter 84-2) that transmits light of wavelengths neighboring the wavelength at which the light quantities have exceeded the upper limit threshold is present on the optical path of the light source 30 (step S302). That is, the variable quantity setting unit 66, with the timing corresponding to the optical filter 84 that lets the light of the wavelength range including the wavelength at which the piece of light quantity information has exceeded the upper limit threshold enter the light guide 24, transmits to the light source driver 48 the setting information for changing the setting of the current adjuster (not illustrated) of the light source 30 to lower the detection signal of the light detector 16. By decreasing the light quantity of the light source 30 in this way, the piece of light quantity information that has exceeded the upper limit threshold becomes lower than the upper limit threshold as shown in FIG. 23C. The operations return to the processing in step S102.

In FIG. 23B, of the portions corresponding to n optical filters 84, only those corresponding to the first to third optical filters 84-1 to 84-3 are shown for simplification of the figure. Regarding rotation amount information, the rotation angle when the first optical filter 84-1 is arranged on the optical path of the light source 30 is set as 0 degrees, for example, and the rotation angle linearly increases as the movable optical filter 78 is driven at a constant velocity by the actuator 86. By storing the relationship between rotation amount information and the optical filters 84 in, for example, the memory 54, the control unit 46 can determine which optical filter 84 is present on the optical path of the light source 30 by the rotation amount information from the rotation measure 88.

Furthermore, when the shape calculating apparatus 10 includes the light detector 90, the control unit 46 can control the light intensity of the light source 30 while confirming whether the intensity of light input to the sensor unit 12 is a desired value by a detection result of the light detector 90.

Figure 24A:
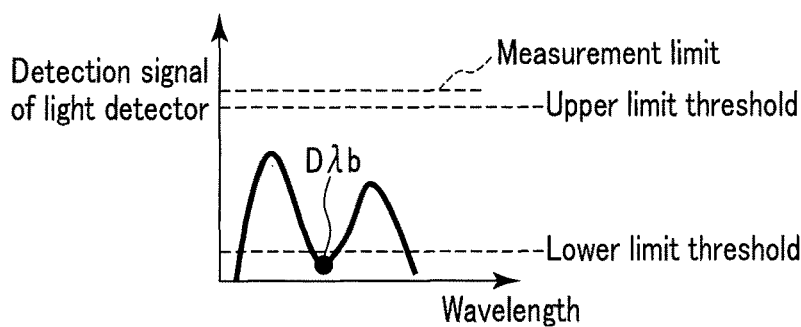
FIG. 24A is a view showing a detection signal of the light detector before a change of variable quantity setting when the detection signal has fallen below a lower limit threshold.

In addition, in step S106, if the determination unit 64 of the control unit 46 determines that a piece of light quantity information to be used for curvature calculation has fallen below the lower limit threshold (e.g., light quantity information Dλb), that is, of the detection signal of the light detector 16, any of the light intensities of the wavelengths to be used for curvature calculation has fallen below the lower limit threshold, as shown in FIG. 24A, for example, the determination unit 64 outputs the information indicative of it to the variable quantity setting unit 66.

Figure 24B:
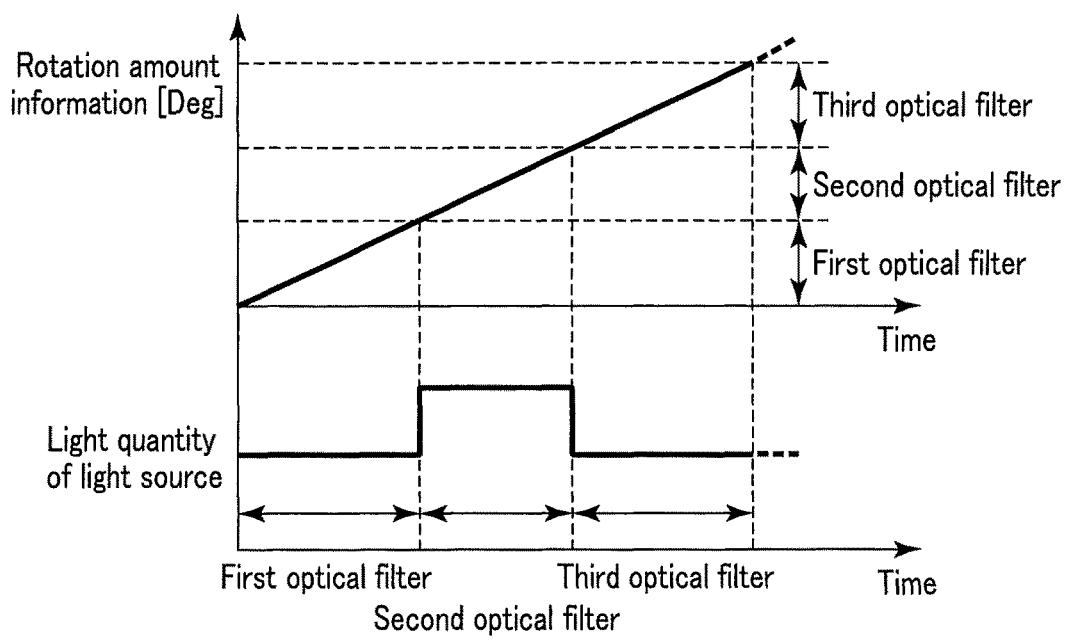
FIG. 24B is a view for describing a method of changing the variable quantity setting by a light intensity change when the detection signal of the light detector has fallen below the lower limit threshold.
Figure 24C:
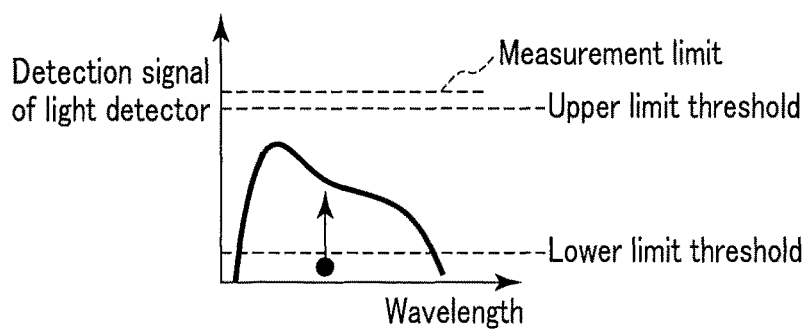
FIG. 24C is a view showing a detection signal of the light detector after the change of the variable quantity setting when the detection signal has fallen below the lower limit threshold.

After receiving the information indicating that at least a piece of light quantity information to be used for curvature calculation has fallen below the lower limit threshold, when the optical filter 84 (e.g., the second optical filter 84-2) that transmits light of wavelengths neighboring the wavelength at which the light quantities have fallen below the lower limit threshold is present on the path of the light source 30, the variable quantity setting unit 66 makes the setting change of increasing the light quantity of the light source 30, as shown in FIG. 24B (step S303). That is, the variable quantity setting unit 66, with the timing corresponding to the optical filter 84 that lets the light of the wavelength range including the wavelength at which the piece of light quantity information has fallen below the lower limit threshold enter the light guide 24, transmits to the light source driver 48 the setting information for changing the setting of the current adjuster (not illustrated) of the light source 30 to raise the detection signal of the light detector 16. By increasing the light quantity of the light source 30 in this way, the piece of light quantity information that has fallen below the lower limit threshold becomes higher than the lower limit threshold as shown in FIG. 24C. The operations return to the processing in step S102. In FIG. 24B, as in FIG. 23B, of the portions corresponding to n optical filters 84, only those corresponding to the first to third optical filters 84-1 to 84-3 are shown for simplification of the figure.

In step S302 and step S303, instead of changing the light intensity of the light source 30, it is also possible to control the velocity of each optical filter 84 that is passing across the optical path of the light source 30, for example, the rotation velocity of the rotatable plate 80 of the movable optical filter 78.

Figure 25A:
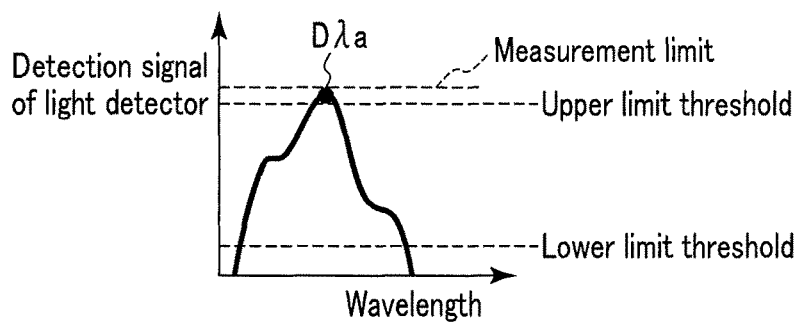
FIG. 25A is a view showing a detection signal of the light detector before a change of variable quantity setting when the detection signal has exceeded an upper limit threshold.
Figure 25B:
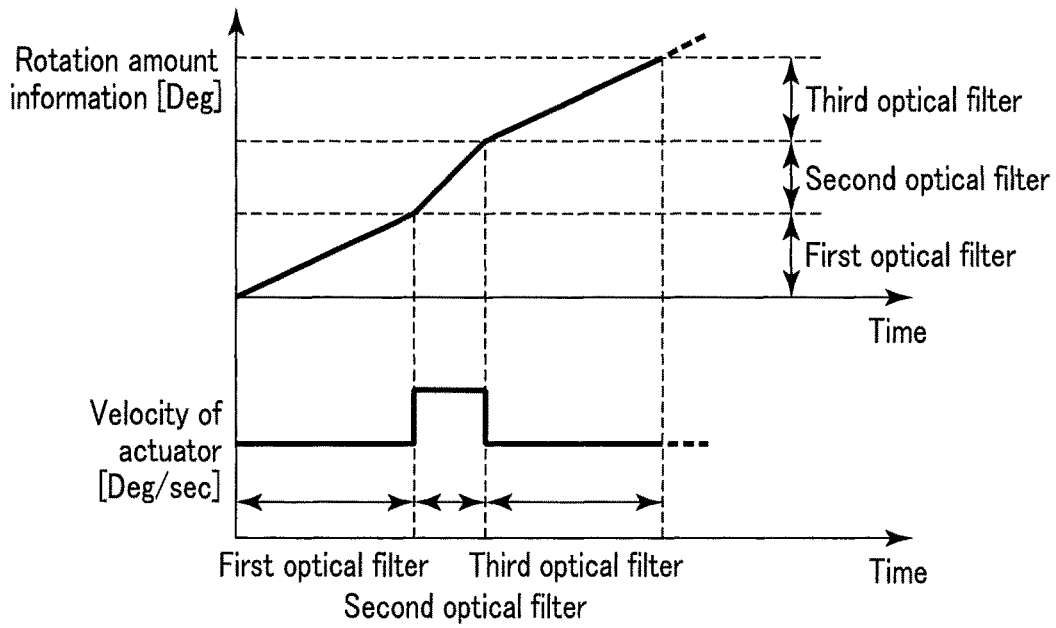
FIG. 25B is a view for describing a method of changing the variable quantity setting by a change of velocity of an actuator when the detection signal of the light detector has exceeded the upper limit threshold.
Figure 25C:
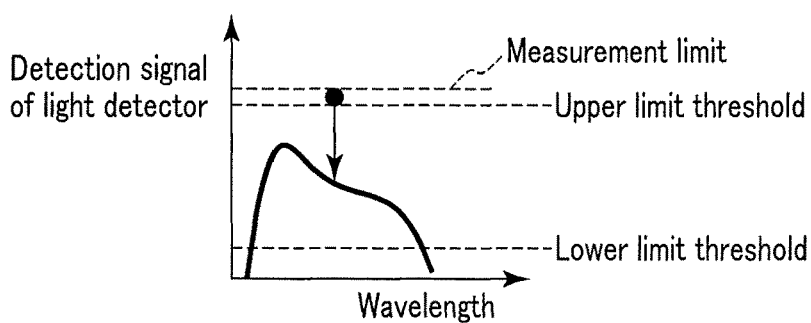
FIG. 25C is a view showing a detection signal of the light detector after the change of the variable quantity setting when the detection signal has exceeded the upper limit threshold.

That is, when a piece of light quantity information to be used for curvature calculation has exceeded the upper limit threshold (e.g., light quantity information Dλa) as shown in FIG. 25A, in step S302, the variable quantity setting unit 66, by shortening the time during which the optical filter 84 (e.g., the second optical filter 84-2) that transmits light of wavelengths neighboring the wavelength at which the light quantities have exceeded the upper limit threshold is present on the optical path of the light source 30, makes the setting change of decreasing the quantity of light of the wavelength range including the wavelength caused to enter the light guide 24 as shown in FIG. 25B. That is, the variable quantity setting unit 66 transmits to the light source driver 48 the setting information for changing a detection signal of the light detector 16 to be lower, by accelerating the rotation velocity of the rotatable plate 80 of the movable optical filter 78 driven by the actuator 86 so that the optical filter 84 that lets the light of the wavelength range including the wavelength at which the piece of light quantity information has exceeded the upper limit threshold enter the light guide 24 is removed from the optical path of the light source 30 earlier than the other optical filters 84 that let the light of the wavelength range including the wavelength at which a piece of light quantity information does not exceed the upper limit threshold enter the light guide 24. By such acceleration of the velocity of the optical filters 84 that are passing across the optical path of the light source by the actuator 86, the piece of light quantity information that has exceeded the upper limit threshold becomes lower than the upper limit threshold as shown in FIG. 25C.

Figure 26A:
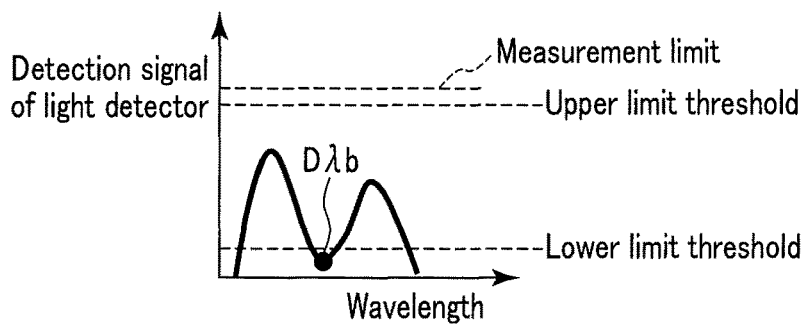
FIG. 26A is a view showing a detection signal of the light detector before a change of variable quantity setting when the detection signal has fallen below a lower limit threshold.
Figure 26B:
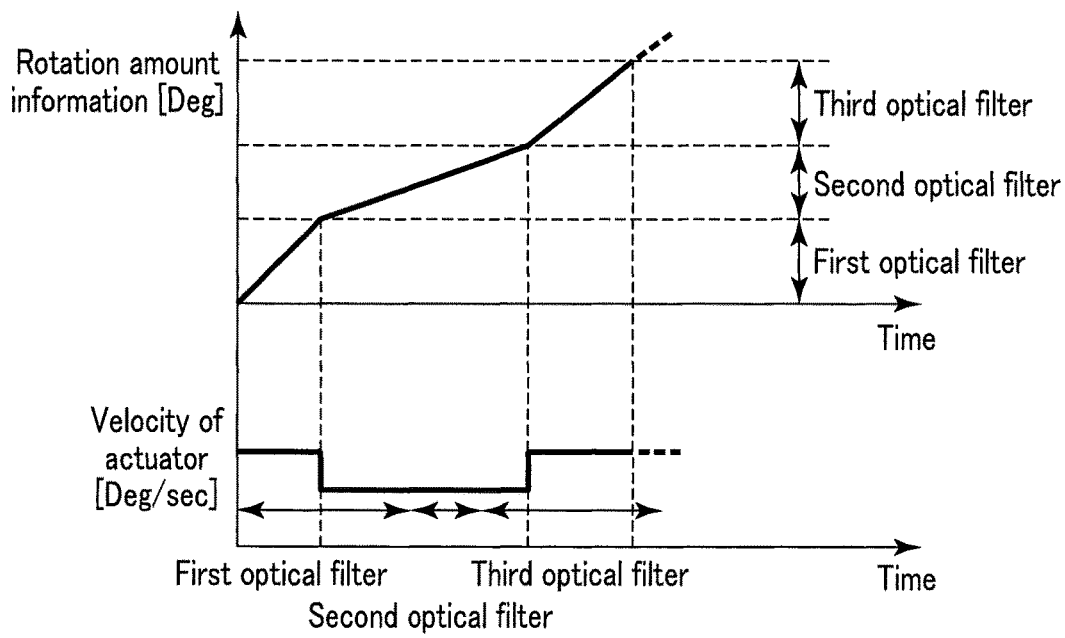
FIG. 26B is a view for describing a method of changing the variable quantity setting by a change of the velocity of the actuator when the detection signal of the light detector has fallen below the lower limit threshold.
Figure 26C:
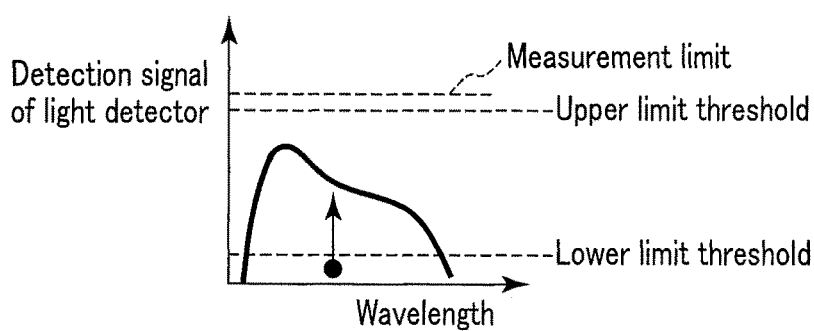
FIG. 26C is a view showing a detection signal of the light detector after the change of the variable quantity setting when the detection signal has fallen below the lower limit threshold.

Also, when a piece of light quantity information to be used for curvature calculation has fallen below the lower limit threshold (e.g., light quantity information Dλb) as shown in FIG. 26A, in step S303, by extending the time during which the optical filter 84 (e.g., the second optical filter 84-2) that transmits light of wavelengths neighboring the wavelength at which the light quantities have fallen below the lower limit threshold is present on the optical path of the light source 30, the variable quantity setting unit 66 makes the setting change of increasing the quantity of light of the wavelength range including the wavelength caused to enter the light guide 24 as shown in FIG. 26B. That is, the variable quantity setting unit 66 transmits to the light source driver 48 the setting information for changing a detection signal of the light detector 16 to be higher, by decelerating the rotation velocity of the rotatable plate 80 of the movable optical filter 78 driven by the actuator 86 so that the optical filter 84 that lets the light of the wavelength range including the wavelength at which the piece of light quantity information has fallen below the lower limit threshold enter the light guide 24 remains on the optical path of the light source 30 longer than the other optical filters 84 that let the light of the wavelength range including the wavelength at which a piece of light quantity information does not fall below the lower limit threshold enter the light guide 24. By such deceleration of the velocity of the optical filters 84 that are passing across the optical path of the light source by the actuator 86, the piece of light quantity information that has fallen below the lower limit threshold becomes higher than the lower limit threshold as shown in FIG. 26C.

In FIGS. 25B and 26B, as in FIG. 23B, of the portions corresponding to n optical filters 84, only those corresponding to the first to third optical filters 84-1 to 84-3 are shown for simplification of the figures.

Instead of changing the light intensity of the light source 30 or the velocity of the optical filters 84 of the movable optical filter 78 that are passing across the optical path of the light source so that the light quantity outside the range of the thresholds gets back into the range of the thresholds, it is also possible to adjust the light intensity of the light source 30 or the velocity of the optical filters 84 that are passing across the optical path of the light source so that the detection signal of the light detector 16 always becomes a fixed value in the entire wavelength region to be used for shape estimation, without providing any threshold, as described in the aforementioned first embodiment.

As described above, the shape calculating apparatus 10 according to the present third embodiment further comprises the movable optical filter 78 mounted with the optical filters 84 that transmits light of wavelengths different from one another, thereby changing the dynamic range of the light intensity of light input to the sensor unit 12 for each wavelength range. It thus is possible to obtain the light quantity information indicating the relationship between the wavelengths and light quantities with a high degree of accuracy from the sensor unit 12 including the detection targets 26, and accurately calculate the shape of each detection target 26.

As the movable optical filter 78, a rotary movable optical filter including the rotation axis 82 can be used.

Here, the shape calculating apparatus 10 further comprises one light source 30 that emits light, and the control unit 46 can change the dynamic range of the intensity of light input to the sensor unit 12 for each predetermined wavelength range, by changing the light intensity of the light source 30 for each optical filter 84 disposed on the optical path from the light source 30 to the sensor unit 12.

Alternatively, the shape calculating apparatus 10 further comprises the actuator 86 that drives the movable optical filter 78, and the control unit 46 can change the dynamic range of the intensity of light input to the sensor unit 12, by controlling the actuator 86 so as to drive at a different velocity for each optical filter 84 mounted on the movable optical filter 78.

The control unit 46 changes the dynamic range of the intensity of light input to the sensor unit 12 by changing the light intensity of the light source 30 or the velocity of the optical filters 84 that are passing across the path of the light source when a measurement result of the light detector 16 has exceeded the upper limit threshold or has fallen below the lower limit threshold.

In addition, the control unit 46 changes the dynamic range of the intensity of light input to the sensor unit 12 by changing the light intensity of the light source 30 or the velocity of the optical filters 84 that are passing across the optical path of the light source so that a measurement result of the light detector 16 can be fixed.

Fourth Embodiment

As described above, in the shape calculating apparatus 10 according to the first embodiment, the dynamic range of light input to the sensor unit 12 is changed for each wavelength range by changing the light intensities of the light sources 30-1, 30-2, . . . , and 30-n. In the shape calculating apparatus 10 according to the second embodiment, the dynamic range of a detection signal generated by the light detector 16 is changed for each wavelength range by changing the exposure time or sensitivity of each pixel sensor 72 of the light detector 16. In the shape calculating apparatus 10 according to the third embodiment, the dynamic range of the intensity of light input to the sensor unit 12 is changed for each wavelength range by means of one light source 30 and the movable optical filter 78.

Two or more of the methods of changing a dynamic range as described in the first to third embodiments can be combined.

The combination of the second and third embodiments will be described as the fourth embodiment, as an example. Here, the differences from the second and third embodiments previously discussed will be described, and the descriptions of the same portions will be omitted by the addition of the same codes.

The basic configuration of the shape calculating apparatus 10 according to the fourth embodiment is the same as the third embodiment as shown in FIG. 27. The light detector 16 includes the line sensor 70 constituted by the pixel sensors 72 that measure the light intensities of wavelength ranges different from one another. Here, one pixel sensor 72 corresponds to one optical filter 84 of the movable optical filter 78. That is, the wavelength range detected by one pixel sensor 72 corresponds one-on-one to the wavelength range of light that is transmitted through one optical filter 84. Alternatively, the pixel sensors 72 may correspond many-on-one to the optical filters 84. That is, the wavelength range of light that is transmitted through one optical filter 84 may contain the wavelength ranges detected by the pixel sensors 72. The many-on-one correspondence is more desirable because an advantageous effect as described in the second embodiment with FIG. 16C can be brought about.

As shown in FIG. 28, the light detector 16 comprises at least one of the each pixel exposure time adjuster 74 that changes the exposure time of each pixel sensor 72 and the each pixel sensitivity adjuster 76 that changes the sensitivity of each pixel sensor 72. Furthermore, the variable quantity setting unit 66 comprised by the control unit 46 of the processor 22 includes a light detector setting unit 92 that sets the exposure time or sensitivity of each pixel sensor 72 of the light detector 16 and a light quantity setting unit 94 that sets the light intensity of one light source 30 of the light source unit 14 or the velocity of the optical filters 84 that are passing across the optical path of the light source.

Figure 29:
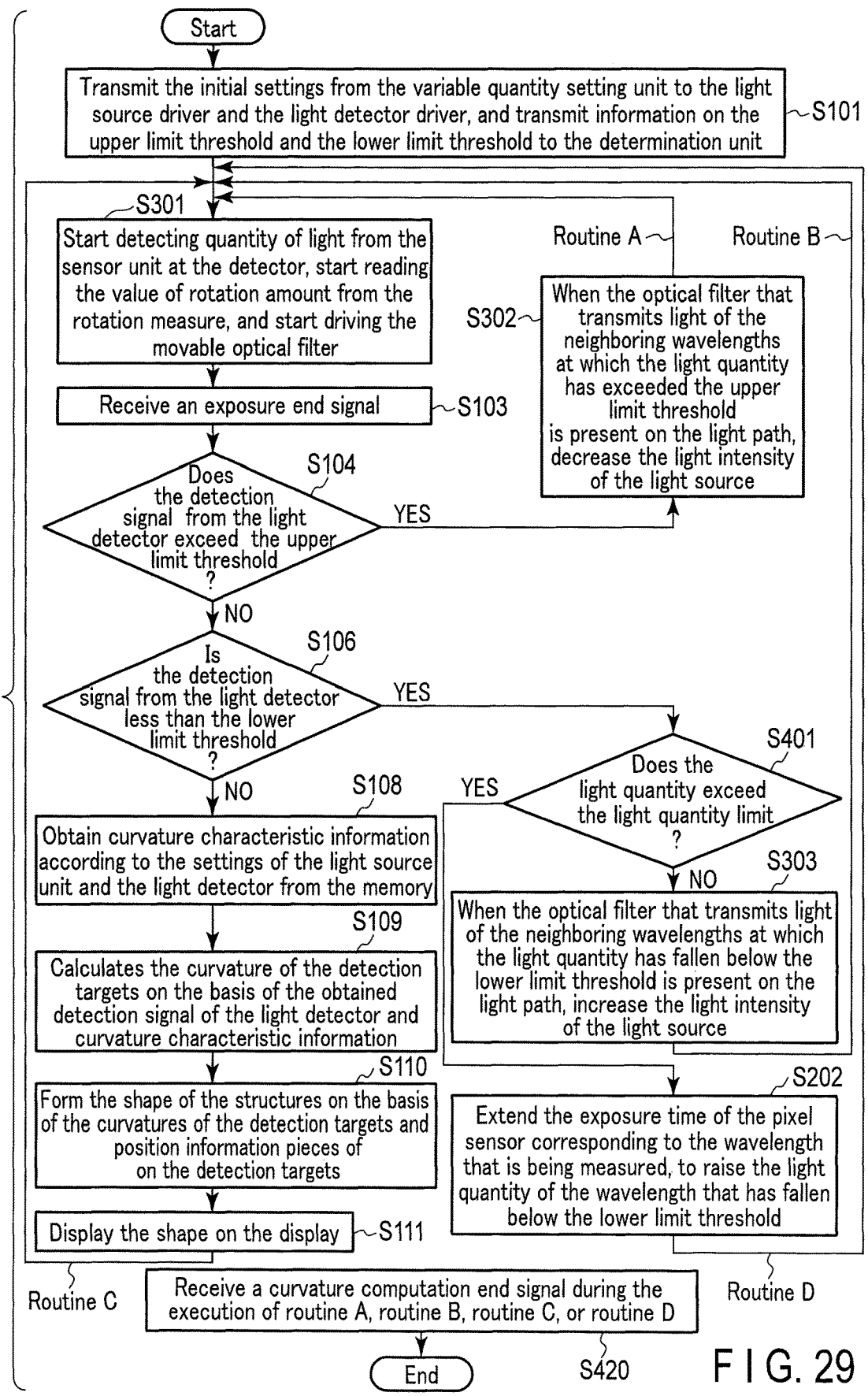
FIG. 29 is an operational flowchart of the shape calculating apparatus according to the fourth embodiment.

Hereinafter the operations of the processor 22 of the shape calculating apparatus 10 according to the present fourth embodiment will be described with reference to the flow-chart of FIG. 29. This flowchart shows an example of a case of proceeding first with the setting of the light intensity of the light source 30 or the velocity of the optical filters 84 that are passing across the optical path of the light source, and proceeding as necessary with the setting of the exposure time or sensitivity of each pixel sensor 72. Of course, the order of the changing methods can be opposite to this, that is, it is possible to proceed first with the setting of the exposure time or sensitivity of each pixel sensor 72, and proceed as necessary with the setting of the light intensity of the light source 30 or the velocity of the optical filters 84 that are passing across the optical path of the light source.

If the input unit 44 receives a curvature computation start signal from the input device 60, the operations of this flowchart are started. Here, the initial setting in step S101, and the routine A composed of step S301, step S103, step S104, and step S302 are the same as the third embodiment. That is, when a piece of light quantity information to be used for curvature calculation has exceeded the upper limit threshold, in step S302, the light quantity setting unit 94 of the variable quantity setting unit 66 makes the setting change of decreasing the light quantity of the light source 30 when the optical filter 84 that transmits light of wavelengths neighboring the wavelength at which the light quantities have exceeded the upper limit threshold is present on the optical path of the light source 30. Alternatively, the light quantity setting unit 94, by shortening the time during which the optical filter 84 that transmits light of wavelengths neighboring the wavelength at which the light quantities have exceeded the upper limit threshold is present on the optical path of the light source 30, makes the setting change of decreasing the quantity of the light of the wavelength range including the wavelength caused to enter the light guide 24.

Figure 30A:
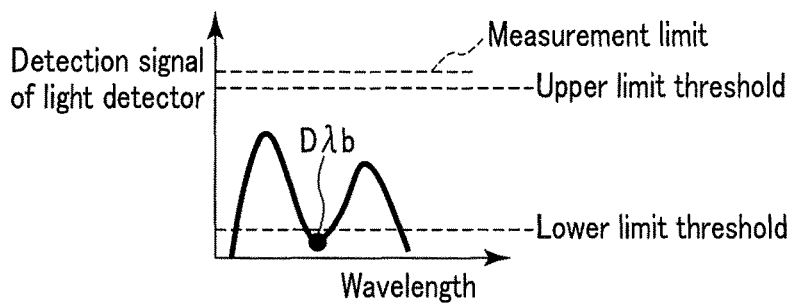
FIG. 30A is a view showing a detection signal of the light detector before a change of variable quantity setting when the detection signal has fallen below a lower limit threshold.
Figure 30B:
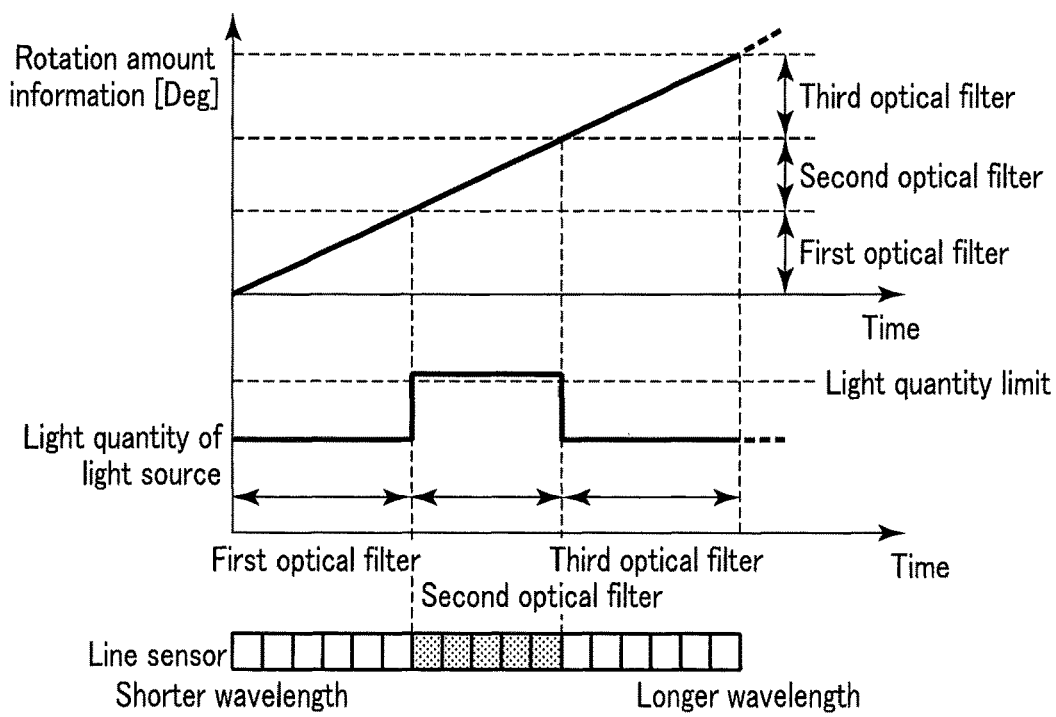
FIG. 30B is a view for describing a method of changing the variable quantity setting by the combination of a light intensity change and an exposure time change when the detection signal of the light detector has fallen below the lower limit threshold.

In contrast, in the routine B composed of step S301, step S103, step S104, step S106, and step S303 as described in the third embodiment, a step is inserted between step S106 and step S303. That is, in step S106, if the determination unit 64 determines that a piece of light quantity information to be used for curvature calculation has fallen below the lower limit threshold (e.g., light quantity information D$\lambda$b) as shown in FIG. 30A, in the present embodiment, the determination unit 64 of the control unit 46 further determines whether or not the light quantity of the light source 30 set regarding the optical filter 84 (e.g., the second optical filter 84-2) that transmits light of wavelengths neighboring the wavelength at which the light quantities have fallen below the lower limit threshold exceeds the light quantity limit as shown in FIG. 30B (step S401). The value of this light quantity limit is, for example, a value made by subtracting the light quantity increased at a time in step S303 from the largest light quantity of the light source 30. That is, in step S401, whether or not current light quantity is set at a value that has not yet reached the largest light quantity of the light source 30, but exceeds the largest light quantity if it is increased to be in a higher stage is determined. If the determination unit 64 determines that the light quantity does not exceed the light quantity limit in step S401, the processing proceeds to step S303, and the light quantity setting unit 94 of the variable quantity setting unit 66 makes the setting change of increasing the light quantity of the light source 30, when the optical filter 84 (e.g., the second optical filter 84-2) that transmits light of wavelengths neighboring the wavelength at which the light quantities have fallen below the lower limit threshold is present on the optical path of the light source 30.

Alternatively, in step S303, the light quantity setting unit 94 of the variable quantity setting unit 66, by extending the time during which the optical filter 84 (e.g., the second optical filter 84-2) that transmits light of wavelengths neighboring the wavelength at which the light quantities have fallen below the lower limit threshold is present on the optical path of the light source 30, makes the setting change of increasing the quantity of the light of the wavelength range including the wavelength caused to enter the light guide 24. However, in this case, in step S401, a determination is made not regarding whether or not the light quantity of the light source 30 exceeds the light quantity limit, but regarding whether or not the time during which the optical filter 84 (e.g., the second optical filter 84-2) is present on the optical path of the light source 30 exceeds the time limit of being able to stay on the optical path.

However, if the determination unit 64 determines that light quantity exceeds the light quantity limit (or a staying time exceeds the time limit) in step S401, the operation in step S202 as described in the second embodiment is carried out. That is, the light detector setting unit 92 of the variable quantity setting unit 66 makes the setting change of extending the exposure times of the pixel sensors 72 corresponding to the optical filter (e.g., the second optical filter 84-2) corresponding to the wavelength range including the wavelength as shown in FIG. 30B. That is, the variable quantity setting unit 66 transmits to the each pixel exposure time adjuster 74 through the light detector driver 50 the setting information for changing the setting of the exposure times of the pixel sensors 72 that measure light of wavelength ranges of the wavelength at which the piece of light quantity information has fallen below the lower limit threshold and wavelengths neighboring the wavelength so as to raise the detection signal components of the pixel sensors 72. The operations return to the processing in step S301.

In step S202, instead of extending the exposure times, raising the sensitivities is, of course, also possible. That is, the light detector setting unit 92 of the variable quantity setting unit 66 may transmit to the each pixel sensitivity adjuster 76 through the light detector driver 50 the setting information for changing the setting of the sensitivities of the pixel sensors 72 corresponding to the optical filter (e.g., the second optical filter 84-2) corresponding to the wavelength range including the wavelength at which the piece of light quantity information has fallen below the lower limit threshold so as to raise the detection signal components of the pixel sensors 72.

Although the case is described with FIG. 30B where the pixel sensors 72 and the optical filters 84 have a many-on-one correspondence, the one-on-one correspondence is, of course, also possible.

Figure 30C:
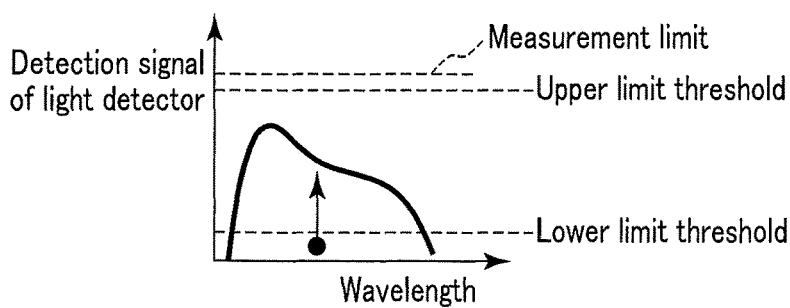
FIG. 30C is a view showing a detection signal of the light detector after the change of the variable quantity setting when the detection signal has fallen below the lower limit threshold.

In such a manner, the routine D composed of step S301, step S103, step S104, step S106, step S401, and step S202 can be repeated. That is, when the detection signal is less than the lower limit threshold even after a setting change, to further raise the detection signal of the light detector 16, the setting of the each pixel exposure time adjuster 74 or the each pixel sensitivity adjuster 76 of the light detector 16 is changed through the light detector driver 50. Thereby, the piece of light quantity information that has fallen below the lower limit threshold becomes higher than the lower limit threshold as shown in FIG. 30C.

If the input unit 44 receives a curvature computation end signal from the input device 60 during the execution of the routine A, routine B, routine C, or routine D (step S420), the processing in this flowchart is terminated.

As described above, the shape calculating apparatus 10 according to the present fourth embodiment comprises the control unit (resolution improving function) of changing the two dynamic ranges of the intensity of light input to the sensor unit 12, and a detection signal of the light detector 16 that is an electrical signal generated by the light detector 16 on the basis of light output from the sensor unit 12. Accordingly, a change by the combination of two or more of the methods of changing a dynamic range can be conducted.

The shape calculating apparatus 10 according to the first to fourth embodiments can be mounted on an endoscope. In the present specification, an endoscope is not restricted to a medical endoscope and an industrial endoscope, but indicates general equipment comprising an insertion section to be inserted into an insertion target.

Hereinafter, an endoscope for medical use will be described as an example of the endoscope.

For example, FIG. 31 illustrates an endoscope system in which the light guide 24 of the shape calculating apparatus 10 according to the embodiment is disposed along an insertion section 96, or a structure body, of an endoscope. This endoscope system includes an endoscope, which is provided with an elongated insertion section 96 that is a structure body to be inserted into a subject (e.g. a body cavity (lumen cavity)), which is an observation target; a handling section 98 coupled to a proximal portion of the insertion section 96; and a connection cable 100. The endoscope system further includes a controller 102 configured to control the endoscope.

Here, the insertion section 96 includes, from the distal side toward the proximal side of the insertion section 96, a distal rigid section, an operation bendable section configured to bend, and a flexible tube section. The distal rigid section is a distal portion of the insertion section 96, and is a rigid member. This distal rigid section is provided with an imager (not shown).

The operation bendable section bends in a desired direction in accordance with an operation by an endoscope operator (a worker such as a doctor) of a bend operation knob provided on the handling section 98. By operating the bend operation knob, the operator bends the operation bendable section. By the bending of the operation bendable section, the position and direction of the distal rigid section are varied, so that an observation target is captured in an observation view field that is an imaging range of the imager. Illumination light is radiated from an illumination window (not shown) provided in the distal rigid section on the captured observation target, and the observation target is illuminated. The operation bendable section is configured with node rings (not shown) being coupled along the longitudinal direction of the insertion section 96. The node rings swing relative to each other, and thereby the operation bendable section bends.

The flexible tube section has a desired flexibility, so as to be bent by external force. The flexible tube section is a tubular member extending from the handling section 98.

The connection cable 100 connects the handling section 98 and controller 102.

The controller 102 executes an image processing on an observation image captured by the imager of the endoscope, so as to cause a display (not shown) to display the observation image that has been subjected to the image processing. In the embodiment, as shown in FIG. 31, the light source 14, light detector 16, light branching element 18, and processor 22 of the shape calculating apparatus 10 are incorporated in the controller 102. The light guide 24 is disposed to extend in the longitudinal axial direction of the insertion section 96 from the controller 102 through the connection cable 100 and handling section 98. The reflection member 28 is provided in the distal rigid section of the insertion section 96. In this case, the detection targets 26 are provided at positions in portions of the light guide 24 that correspond to the operation bendable section and flexible tube section of the insertion section 96.

In the meantime, the structure body is not limited to this endoscope and may be various probes, catheters, oversheaths (tubes used in assisting the insertion of endoscopes, catheters, etc.), and the like.

Additional advantages and modifications will readily occur to those skilled in the art. Therefore, the invention in its broader aspects is not restricted to the specific details and representative embodiments shown and described herein. Accordingly, various modifications may be made without departing from the spirit or scope of the general inventive concept as defined by the appended claims and their equivalents.

What is claimed is:

1. A shape calculating apparatus comprising:
a light source configured to emit light, the light source comprising optical filters configured to change an intensity of a light quantity for each of a plurality of wavelength ranges;
a light guide disposed in a structure to be a target for shape calculation, the light guide being configured to guide the light emitted from the light source;
detection targets disposed in the light guide in a longitudinal direction of the light guide, the detection targets having a light absorption spectra different from one another, the detection targets being configured to absorb light guided by the light guide according to a bend shape of the light guide to decrease light quantity;
a sensor configured to detect light quantity information in wavelengths included in the light absorption spectra in the light guided by the light guide, and the sensor being configured to output a detection signal; and
a controller comprising hardware, the controller being configured to:
 make a calculation relating to a shape of each of the detection targets based on the light quantity information; and
 change, using the optical filters, a dynamic range of at least one of an intensity of light input to the light guide and the detection signal output by the sensor for each of predetermined wavelength ranges so that a magnitude of the detection signal is within a range between a lower limit threshold relating to a lower detection limit of the sensor and an upper limit threshold relating to an upper detection limit of the sensor.

2. The shape calculating apparatus according to claim 1, wherein
the light source comprises a plurality of light sources configured to change light intensities of emitting light independently of one another, and
the controller is configured to change a dynamic range of an intensity of light input to the light guide by changing light intensities of the plurality of light sources.

3. The shape calculating apparatus according to claim 2, wherein the plurality of light sources differ from one another in optical frequency spectrum.

4. The shape calculating apparatus according to claim 3, wherein the plurality of light sources comprise at least one a laser light source.

5. The shape calculating apparatus according to claim 3, wherein the plurality of light sources are different in optical frequency spectrum so as to cover an entire wavelength region to be used for shape estimation.

6. The shape calculating apparatus according to claim 3, wherein the plurality of light sources are different in optical frequency spectrum so as to sufficiently change light intensities of frequencies of light to be used for shape estimation.

7. The shape calculating apparatus according to claim 2, wherein the controller is configured to make a change by a combination of two or more of methods of changing the dynamic range.

8. The shape calculating apparatus according to claim 1, wherein the optical filters are different in optical frequency spectrum so as to cover an entire wavelength region to be used for shape estimation.

9. The shape calculating apparatus according to claim 1, wherein the optical filters are different in optical frequency spectrum so as to sufficiently change light intensities of frequencies of light to be used for shape estimation.

10. The shape calculating apparatus according to claim 1, wherein an absorbance of the optical filters is equal to an absorbance used for a detection target of the sensor.

11. The shape calculating apparatus according to claim 1, wherein the optical filters are disposed on optical paths from the light source toward the sensor.

12. The shape calculating apparatus according to claim 1, wherein the sensor comprises pixel sensors that respectively measure quantities of light of different wavelengths, and the controller is configured to:
when the measured light quantity of light is below a lower limit threshold, the controller repeatedly sums up measurement values of each pixel sensor of the pixel sensors; and
adjusts the number of times the measurement values are summed up to obtain a total value.

13. The shape calculating apparatus according to claim 1, wherein the controller is configured to change the dynamic range when a measurement result of the sensor has exceeded the upper limit threshold or has fallen below the lower limit threshold.

14. The shape calculating apparatus according to claim 1, wherein the controller is configured to change the dynamic range so that a measurement result of the sensor is fixed.

15. The shape calculating apparatus according to claim 1, wherein
the light source contains two or more light sources that each emit light,
the detection targets are optical characteristic changing materials that exert influences different from one another on a spectrum of light guided by the light guide, and
the sensor is configured to detect light that is guided by the light guide and influenced by the optical characteristic changing materials, and outputs the light quantity information.

16. The shape calculating apparatus according to claim 1, wherein the sensor comprises pixel sensors that respectively measure quantities of light of different wavelengths, and the controller is configured to change a dynamic range of the detection signal for each of the predetermined wavelength ranges by changing exposure times or sensitivities of the pixel sensors.

17. The shape calculating apparatus according to claim 16, wherein the controller is configured to change the exposure time or the sensitivity for each of the pixel sensors so that a measurement result is between an upper limit threshold and a lower limit threshold that have been set.

18. The shape calculating apparatus according to claim 17, wherein the controller is configured to:
change one of the exposure times or the sensitivities of a first pixel sensor corresponding to a wavelength at which the light quantity has exceeded the upper limit threshold or a wavelength at which the light quantity has fallen below the lower limit threshold, and
change one of the exposure times or the sensitivities of a second pixel sensor corresponding to a wavelength within a predetermined wavelength range of the first pixel sensor.

19. The shape calculating apparatus according to claim 16, wherein each pixel sensor has an upper limit time of a configurable exposure time, and the controller does not change an exposure time equal to or longer than the upper limit time.

20. The shape calculating apparatus according to claim 1, further comprising a movable optical filter mounted with the optical filters.

21. The shape calculating apparatus according to claim 20, wherein the movable optical filter is a rotary movable optical filter including a rotation axis.

22. The shape calculating apparatus according to claim 20, wherein the controller is configured to change a dynamic range of an intensity of light input to the light guide for each of the predetermined wavelength ranges by changing a light intensity of the light source for each of the optical filters disposed on the optical paths from the light sources to the sensor.

23. The shape calculating apparatus according to claim 20, further comprising an actuator that drives the movable optical filter,
wherein the controller is configured to change a dynamic range of an intensity of light input to the light guide by controlling the actuator to drive at a different velocity for each of the optical filters mounted on the movable optical filter.

24. An endoscope system comprising:
an endoscope comprising an insertion section configured to be inserted into a subject;
a controller connected to the endoscope; and
the shape calculating apparatus according to claim 15,
wherein the light guide is provided in the insertion section of the endoscope, and the controller calculates a shape of the insertion section of the endoscope based on the light quantity information.

25. A shape calculating apparatus comprising:
a light source configured to emit light;
a light guide disposed in a structure to be a target for shape calculation, the light guide being configured to guide the light emitted from the light source;
detection targets disposed in the light guide in a longitudinal direction of the light guide, the detection targets having a light absorption spectra different from one another, the detection targets being configured to absorb light guided by the light guide according to a bend shape of the light guide to decrease light quantity;
a sensor configured to detect light quantity information in wavelengths included in the light absorption spectra in the light guided by the light guide, and the sensor being configured to output a detection signal; and
a controller comprising hardware, the controller being configured to:
make a calculation relating to a shape of each of the detection targets based on the light quantity information; and
change, using the optical filters, a dynamic range of at least one of an intensity of light input to the light guide and the detection signal output by the sensor for each of predetermined wavelength ranges so that a magnitude of the detection signal is within a range between a lower limit threshold relating to a lower detection limit of the sensor and an upper limit threshold relating to an upper detection limit of the sensor;
wherein the sensor comprises pixel sensors that respectively measure quantities of light of different wavelengths, and the controller is configured to change a dynamic range of the detection signal for each of the predetermined wavelength ranges by changing exposure times or sensitivities of the pixel sensors; and
each pixel sensor has an upper limit time of a configurable exposure time, and the controller does not change an exposure time equal to or longer than the upper limit time.

* * * * *